(12) United States Patent
Appel et al.

(10) Patent No.: US 12,144,862 B2
(45) Date of Patent: Nov. 19, 2024

(54) ANTIBODY BIOPHARMACEUTICAL FORMULATIONS INCLUDING POLYMER EXCIPIENTS

(71) Applicant: The Board of Trustees of the Leland Stanford Junior University, Palo Alto, CA (US)

(72) Inventors: Eric A. Appel, Palo Alto, CA (US); Joseph L. Mann, Mountain View, CA (US); John Klich, Freehold, NJ (US); Catherine M. Kasse, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 18/200,958

(22) Filed: May 23, 2023

(65) Prior Publication Data
US 2023/0372488 A1    Nov. 23, 2023

Related U.S. Application Data

(60) Provisional application No. 63/344,927, filed on May 23, 2022.

(51) Int. Cl.
*A61K 47/32*     (2006.01)
*C07K 16/10*    (2006.01)

(52) U.S. Cl.
CPC .......... *A61K 47/32* (2013.01); *C07K 16/1063* (2013.01)

(58) Field of Classification Search
None
See application file for complete search history.

(56) References Cited

U.S. PATENT DOCUMENTS

| | | |
|---|---|---|
| 5,415,864 A | 5/1995 | Kopecek et al. |
| 6,369,027 B1 | 4/2002 | Boyle et al. |
| 7,160,970 B2 | 1/2007 | Creamer et al. |
| 7,309,593 B2 | 12/2007 | Ofstead et al. |
| 7,462,363 B2 | 12/2008 | Braun et al. |
| 7,829,317 B2 | 11/2010 | Ofstead et al. |
| 7,989,401 B2 | 8/2011 | Kurian et al. |
| 8,048,258 B2 | 11/2011 | Kurimura et al. |
| 8,129,159 B2 | 3/2012 | Ofstead et al. |
| 9,526,687 B2 | 12/2016 | Klug et al. |
| 9,790,381 B2 | 10/2017 | Arila et al. |
| 10,717,799 B2 | 7/2020 | Tale et al. |
| 11,021,620 B2 | 6/2021 | Herlihy |
| 11,021,622 B2 | 6/2021 | Kim et al. |
| 11,535,840 B2 | 12/2022 | Kaar et al. |
| 11,945,892 B2 | 4/2024 | Appel et al. |
| 2005/0107546 A1 | 5/2005 | Creamer et al. |
| 2005/0277739 A1 | 12/2005 | Yang et al. |
| 2006/0269490 A1 | 11/2006 | Braun et al. |
| 2009/0124707 A1 | 5/2009 | Tamori et al. |
| 2010/0016506 A1 | 1/2010 | Tamori et al. |
| 2010/0204424 A1 | 8/2010 | Tamori et al. |
| 2014/0086854 A1 | 3/2014 | Klug et al. |
| 2014/0328918 A1 | 11/2014 | Fetzer |
| 2015/0159009 A1 | 6/2015 | Lau |
| 2017/0038500 A1* | 2/2017 | Benz ................... G02B 1/043 |
| 2018/0066091 A1 | 3/2018 | Tale et al. |
| 2018/0273658 A1 | 9/2018 | Iwasaki |
| 2018/0296680 A1 | 10/2018 | Webber et al. |
| 2019/0358341 A1 | 11/2019 | Adams et al. |
| 2020/0113816 A1 | 4/2020 | Bellan |
| 2022/0125886 A1 | 4/2022 | Appel et al. |
| 2023/0108947 A1 | 4/2023 | Apple et al. |
| 2023/0372488 A1 | 11/2023 | Appel et al. |
| 2024/0067767 A1 | 2/2024 | Appel et al. |

FOREIGN PATENT DOCUMENTS

| | | |
|---|---|---|
| CN | 1693326 A | 11/2005 |
| CN | 1869080 A | 11/2006 |
| CN | 103492437 A | 1/2014 |
| CN | 107406556 A | 11/2017 |
| CN | 107629767 A | 1/2018 |
| JP | H11503616 A | 3/1999 |
| JP | 2014-227384 A | 12/2014 |
| JP | 2019 142787 A | 8/2019 |

(Continued)

OTHER PUBLICATIONS

Akimoto et al. (2018), Controlled aggregation behavior of thermoresponsive polyremic micelles by introducing hydrophilic segments as corona components. J. Polym. Sci. Part A: Polym. Chem., 56: 1695-1704 (Year: 2018).

(Continued)

*Primary Examiner* — Melissa S Mercier
(74) *Attorney, Agent, or Firm* — Rudy J. Ng; Bozicevic, Field & Francis LLP

(57) ABSTRACT

Polyacrylamide-based copolymers act as stabilizing excipients in formulations of antibody biopharmaceutical agents without interacting directly with the antibody or altering its pharmacokinetic properties. The polyacrylamide-based copolymers confer a substantial stability benefit to high concentration compositions of a variety of antibodies by precluding adsorption of the antibody to the interfaces of the composition, preventing undesirable aggregation events and maintaining the binding activity of the antibody. Such antibody compositions are useful in methods of administering the composition to a subject.

30 Claims, 11 Drawing Sheets

(56) References Cited

FOREIGN PATENT DOCUMENTS

| WO | WO 1997/023614 A1 | 7/1997 | | |
|---|---|---|---|---|
| WO | WO 2001/005578 A1 | 1/2001 | | |
| WO | WO 2003/066791 A1 | 8/2003 | | |
| WO | WO 2009/034958 A1 | 3/2009 | | |
| WO | WO 2000/046262 A1 | 8/2010 | | |
| WO | WO 2012/119746 A1 | 9/2012 | | |
| WO | WO 2013/024800 A1 | 2/2013 | | |
| WO | WO 2016/140845 A1 | 9/2016 | | |
| WO | WO 2018/112313 A1 | 6/2018 | | |
| WO | WO2018112551 | 6/2018 | | |
| WO | WO 2020/076963 A1 | 4/2020 | | |
| WO | WO 2021/119607 A1 | 6/2021 | | |
| WO | WO 2021/142391 A1 | 7/2021 | | |
| WO | WO2021211976 | 10/2021 | | |
| WO | WO-2021211976 A2 * | 10/2021 | ........... | A61K 9/1272 |
| WO | WO 2023/230046 A1 | 11/2023 | | |
| WO | WO 2024/015644 A1 | 1/2024 | | |

OTHER PUBLICATIONS

Chan et al. Combinatorial Polyacrylamide Hydrogels for Preventing Biofouling on Implantable Biosensors. bioRxiv; 2020. (Year: 2020).

Chiklis, C. et al. Swelling of Thin Films. I. Acrylamide-N-Isopropylacrylamide Copolymers in Water, Journal of Polymer Science, pp. 1617-1626, 1970.

Gu et al. Combinatorial synthesis with high throughput discovery of protein-resistant membrane surfaces. Biomaterial, vol. 34, Issue 26, 2013, pp. 6133-6138. (Year: 2013).

International Search Report and Written Opinion, Patent Cooperation Treaty Application No. PCT/US2023/023257, Aug. 9, 2023, 8 pages.

Kye et al. Tunable Temperature Response of a Thermochromic Photonic Gel Sensor Containing N-Isopropylacrylamide and 4-Acryloyilmorpholine. Sensors (Basel). Jun. 15, 2017;17(6):1398 (Year: 2017).

Maikawa, C.L., el al., Egineering biopharmaeutical formulations to improve diabetes management, Science Translational Medicine, vol. 13, 11 pages, Jan. 27, 2021.

Mann, J., et al. An Ultrafast Insulin Formulation Enabled by High-Throughput Screening of Engineered Polymeric Excipients, Science Translational Medicine, 12 pages, Jul. 2020 vol. 12.

Tang et al. Temperature-Responsive Polymer Modified Surface for Cell Sheet Engineering. Polymers 2012, 4, 1478-1498. (Year: 2012).

Tuncel, A. et al., A Novel Approach for Albumin Determination in Acqueos Media by Using Temperature- and pH-Sensitive N-Isopropylacrylamide-co-N-[3-(dimelhylamino)-propyl]methacrylamide Random Copolymers, Chemical Engineering Department, Hacetlepe University, May 17, 2021, pp. 2060-2071.

Webber, M.J., et al., Supramolecular PEGylation of biopharmaceuticals, Proc. Nat. Acad. Sci., Dec. 13, 2016, vol. 113, No. 50, 14189-14194.

* cited by examiner

ANTIBODY BIOPHARMACEUTICAL FORMULATIONS INCLUDING POLYMER EXCIPIENTS

RELATED APPLICATIONS

This application claims the benefit of the priority of U.S. Provisional Application No. 63/344,927, filed May 23, 2022, which is incorporated herein by reference in its entirety.

BACKGROUND

Antibodies present immense promise in modern pharmacotherapy. These biopharmaceuticals tend to aggregate in formulations, thus requiring low concentration drug formulations, and/or resulting in poor stability. While the mechanism of aggregation varies slightly from antibody to antibody, many antibodies contain hydrophobic patches and/or can partially denature to reveal hydrophobic segments of the molecule that drive absorption of these proteins onto interfaces (e.g., air-water, glass-water, or rubber-water interfaces). The high local concentrations of the protein molecules at these interfaces, coupled with interface-mediated partial unfolding, can trigger initial nucleation of aggregation events that make way for further aggregation. This tendency of antibodies to aggregate at interfaces typically increases with formulation concentrations, negatively impacting overall formulation stability. These inherent concentration limitations often require that large-volume, low-concentration transfusions of antibody therapies are delivered intravenously. However, IV administration places a burden on patients, often requiring lengthy transfusion procedures and access to clinical infrastructure, precluding large numbers of at-risk populations from effective treatments.

These limitations are particularly detrimental for clinical indications in patients that require maintenance of high antibody serum concentrations for therapeutic benefit. For example, broadly neutralizing HIV antibodies (HIV bnAbs) are a class of antibody therapeutics specifically targeting highly conserved regions on the HIV envelope trimer. HIV bnAbs are currently being explored for their use in prophylactic infection prevention and disease management through passive immunization. While the use of bnAbs for HIV prevention and treatment has been demonstrated in mice and non-human primates, bnAb formulations are typically administered by IV infusion to reach the high serum concentrations required for protection against breakthrough infection and to prevent onset of drug resistance. Given the approximately 38 million people currently living with HIV, the 1.7 million new annual infections, and the 690,000 annual AIDS-related deaths globally, development of new therapeutics for the treatment and prevention of HIV that can be deployed even in resource limited settings in lower-to-middle income countries remains a high priority.

Many commercial excipients have been used in trying to overcome challenges associated with high-concentration formulation of antibodies, the most well documented of which in biopharmaceutical formulations are polyoxyethylene-based surfactants such as polysorbates and poloxamers. Despite their widespread use, these systems are still limited by their critical micelle concentrations (the concentration above which the excipient will form micelles, further destabilizing the formulation through introducing large hydrophobic surfaces), possible toxicity through oxidative degradation, and undesirable interaction between the excipient and the cargo in the bulk.

Accordingly, there is a need for improved antibody formulations.

SUMMARY

Compositions including an antibody and a polyacrylamide-based copolymer are provided. Such polyacrylamide-based copolymers can be used as stabilizing excipients in formulations of antibody biopharmaceutical agents without interacting directly with the antibody or altering its pharmacokinetic properties. These polyacrylamide-based copolymers can be generally applied to confer a substantial stability benefit to high concentration compositions of a variety of antibodies, by precluding adsorption of the antibody to the interfaces of the composition, thereby preventing undesirable aggregation events, and maintaining the binding activity of the antibody. In some embodiments, the composition is formulated at an antibody concentration that provides for subcutaneous (SC) injection to a patient which can be conducted in a low resource setting, in contrast, for example, to IV administration.

Also provided are methods of using the antibody compositions, including methods of administering the composition to a human subject in need thereof via injection, e.g., subcutaneously.

DETAILED DESCRIPTION OF EMBODIMENTS

Figure 1:
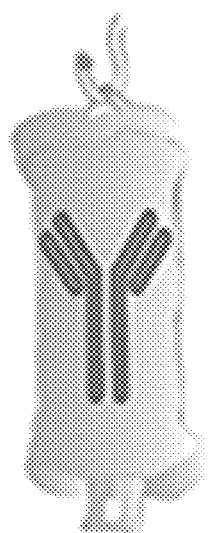
FIG. 1 is a set of schematics showing an overview of stabilization of high-concentration antibody formulations using novel copolymer excipients. (Panel A) Schematic overview of current therapeutic routes of administration for biopharmaceuticals, whereby intravenous administration is common because of limitations on stability of biopharmaceutics at the high concentrations required for subcutaneous administration, resulting in high patient burden. (Panel B) Graphical representation of amphiphilic acrylamide carrier/dopant co-polymer (AC/DC) excipients, such as poly(acryloylmorpholine-co-N-isoproylacrylamide) (MoNi), that can be used to stabilize biopharmaceuticals in formulation. (Panel C) Schematic showing stabilization of monoclonal antibodies in formulation using AC/DC copolymers as a "drop-in" excipient. AC/DC copolymers are amphiphilic and can preferentially absorb to interfaces, precluding antibody interfacial adsorption in formulation and thereby preventing interface-related destabilization and aggregation events.
Figure 1:
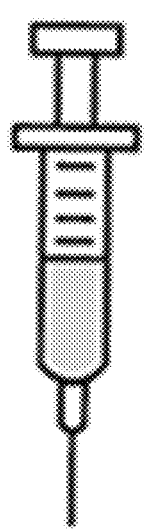
Figure 1:
Figure 1:
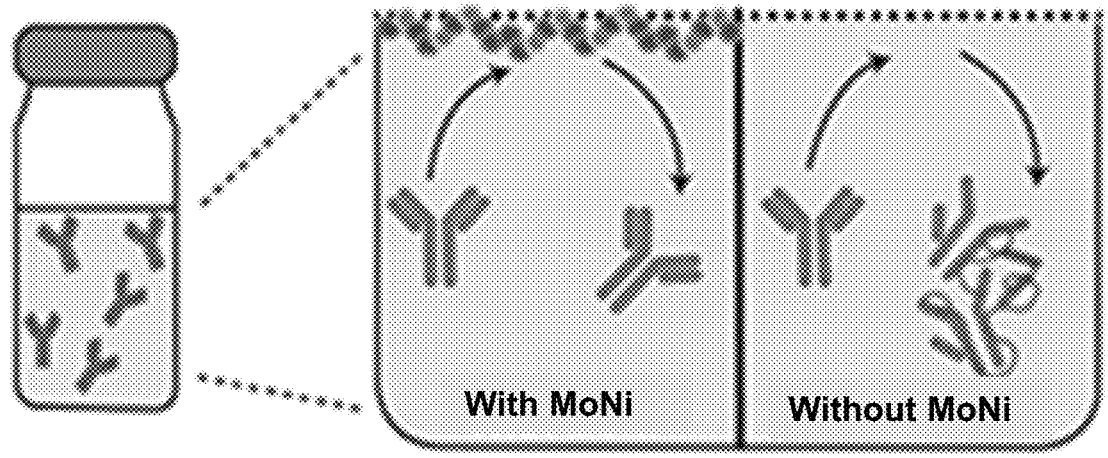

Compositions including an antibody and a polyacrylamide-based copolymer are disclosed herein. In some embodiments, the antibody is present in a stable composition at a high concentration, e.g., 5 wt % or more, such as 7, 10, 12, 15, 20, or 25 wt % or more; or 5, 7, 10, or 12 wt % to 15, 20, or 25 wt %, such as 5-25 wt %, 5-20 wt %, 5-15 wt %, 10-25 wt %, 10-20 wt %, or 15-25 wt %. In some embodiments, the compositions provide a higher concentration and stability of a therapeutic antibody as compared to a conventional, or currently approved antibody formulation. In some embodiments, the antibody is present in the composition substantially in a monomeric association state. In some embodiments, the composition is storage stable. In some embodiments, the composition is formulated for subcutaneous administration of a therapeutically effective amount of the antibody.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Compositions

Aspects of this disclosure include compositions including a polyacrylamide-based copolymer and an antibody. The incorporation of the polyacrylamide-based copolymer into the composition can prevent or reduce aggregation of the antibody, thereby maintaining the biological activity of the antibody, e.g., a specific binding to an antigen.

As used herein, the term "association state," used in reference to an antibody, describes the extent of aggregation of the antibody. For example, non-aggregated antibodies present in a composition can be referred to as monomeric antibodies, or antibodies present in a monomeric association state. In another example, aggregates of two or more antibodies present in a composition can be referred to as aggregated antibodies, or antibodies present in an aggregated association state.

The term "substantially in a monomeric association state," used in reference to an antibody composition, refers to compositions in which 50% or more, e.g., 60% or more, 70% or more, 80% or more, 90% or more, 95% or more, or 97% or more of the antibodies therein are present in a monomeric association state. The term "stability," used in reference to an antibody composition, refers to the ability of the composition to retain at least a portion of binding activity of the antibodies therein over time. For example, a "stable" composition can, in some embodiments, retain 70% or more (e.g., 80% or more, 90% or more, or 95% or more) of a binding activity of an antibody therein over 21 days or more of continuous stressed aging (e.g., based upon half-maximal inhibitory concentration as determined by an enzyme-linked immunosorbent assay).

In some embodiments, the compositions are suitable for subcutaneous injection, e.g., sterile. In some embodiments, the composition is formulated for subcutaneous injection, having a high concentration of antibody (e.g., 5 wt % or more, as described above) and one or more physical properties suitable to be injectable under clinically relevant injection conditions (e.g., a viscosity of 0.2 Pa*s*m or less, such as 0.15, 0.1, or 0.05 Pa*s*m).

In some embodiments, the composition has a surface tension of 60 nM/m or less, for example, 55, 50, 45, 40, 30, or 25 nM/m or less.

Figure 3:
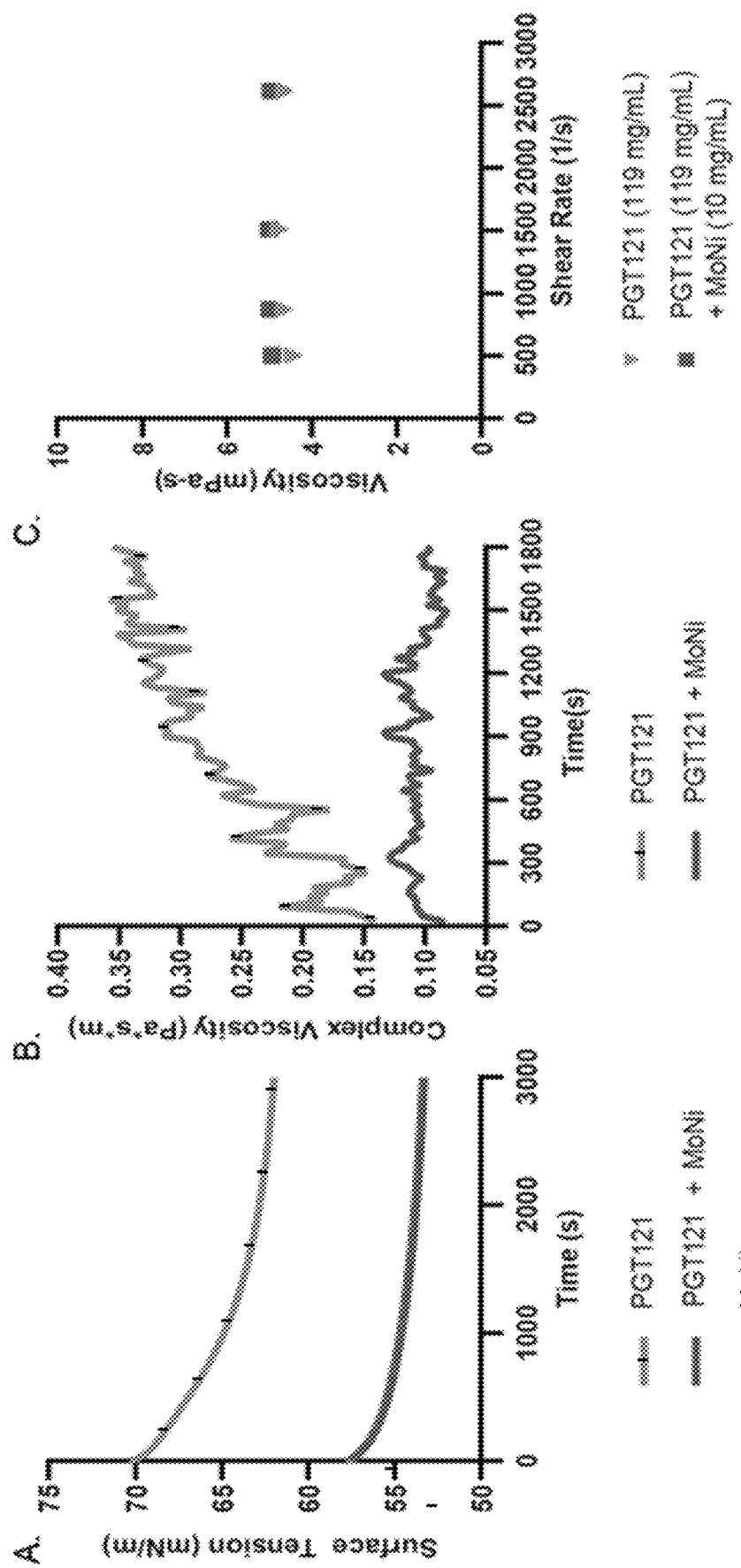
FIG. 3 is a set of graphs showing interfacial interactions of the MoNi polymer excipient in mAb formulations. (Panel A) Comparison of PGT121 (0.2 mg/mL) with and without MoNi (0.1 mg/mL) in time resolved surface tension measurements (n=3). (Panel B) Interfacial rheology measurements (n=3) of PGT121 (0.2 mg/mL) with and without MoNi (0.1 mg/mL). (Panel C) High shear rate viscosity measurements collected at steady state by viscometry experiments for high-concentration formulations of PGT121 (119 mg/mL) with and without MoNi (10 mg/mL).

In some embodiments, the composition has an interfacial complex viscosity of 0.2 Pa·s·m or less, for example, 0.15 Pa·s·m or less, or 0.1 or less. Interfacial complex viscosity (also referred to as interfacial shear viscosity or interfacial complex shear viscosity) is a measure of the flow of molecules present at the interface between a gas and a liquid or at the interface between two immiscible liquids. FIG. 3, Panel B, shows interfacial shear viscosity measurements of an exemplary antibody composition versus a control solution. The exemplary polyacrylamide-based copolymer reduced the interfacial complex viscosity of the resulting antibody composition by 3-fold.

In some embodiments, the composition has a high shear rate viscosity of 6 mPa·s or less, for example, 5.5 mPa·s or less, at shear rates of from 0 $s^{-1}$ to 3,000 $s^{-1}$. FIG. 3, Panel C, shows a graph of the viscosity of an exemplary antibody composition at high shear rates representative of injection, versus a control solution. The exemplary antibody composition including the polyacrylamide-based copolymer exhibited bulk solution viscosity at high shear rates suitable for injection.

In some embodiments, the composition is capable of retaining 70% or more, for example, 75% or more, 80% or more, 85% or more, 90% or more, or 95% or more of a specific binding activity of the antibody for a target epitope or antigen, e.g., as assessed over 21 days of continuous stressed aging. In some embodiments, the binding activity is determined by an enzyme-linked immunosorbent assay.

Polyacrylamide-Based Copolymers

The term "polyacrylamide-based copolymer" refers to a polymer that is formed from the polymerization of two or more distinct monomers, in which at least one of the monomers possesses an acrylamide functional group (i.e., acrylamide monomer). In some embodiments, the polyacrylamide-based copolymer is formed from the polymerization of two structurally different acrylamide monomers (two structurally different monomers that each possess an acrylamide functional group). Polyacrylamide-based copolymers are described in International Publication No. WO 2021/211976 (PCT/US2021/027693), which is incorporated herein by reference in its entirety.

The resulting copolymer can be an alternating copolymer wherein the monomer species are connected in an alternating fashion; a random copolymer, wherein the monomer species are connected to each other within a polymer chain without a defined pattern; a block copolymer, wherein polymeric blocks of one monomer species are connected to polymeric blocks made up of another monomer species; and graft copolymer, wherein the main polymer chain consists of one monomer species, and polymeric blocks of another monomer species are connected to the main polymer chain as side branches (also referred to as sidechains). In some embodiments, the polyacrylamide-based copolymers of the present disclosure are random copolymers.

An "acrylamide monomer," refers to a monomer species that possesses an acrylamide functional group. The term "acrylamide monomer" includes not only monomeric acrylamide, but derivatives of monomeric acrylamide. Examples of acrylamide monomers include, but are not limited to, acrylamide (AM), N-(3-methoxypropoyl)acrylamide (MPAM), 4-acryloylmorpholine (MORPH), N,N-dimethylacrylamide (DMA), N-hydroxyethyl acrylamide (HEAM), N-[tris(hydroxymethyl)-methyl]acrylamide (TRI), 2-acrylamido-2-methylpropane sulfonic acid (AMP), (3-acrylamidopropyl)trimethylammonium chloride (TMA), N-isopropylacrylamide (NIP), N,N-diethylacrylamide (DEA), N-tert-butylacrylamide (TBA), and N-phenylacrylamide (PHE).

In some embodiments, the polyacrylamide-based copolymer of the compositions of the present disclosure is amphiphilic. In some embodiments, the polyacrylamide-based copolymers are co-polymers of two acrylamide monomers, a water-soluble carrier monomer and a functional dopant monomer. In some embodiments, the polyacrylamide-based copolymer is formed via a random polymerization of a water-soluble carrier monomer and a functional dopant monomer.

As used herein, the term "water-soluble carrier monomer" refers to an acrylamide monomer species that is the water-soluble monomer species within the polyacrylamide-based copolymer. In some embodiments, the water-soluble carrier monomer is the predominant hydrophilic species within the polyacrylamide-based copolymer. In some embodiments, the water-soluble carrier monomer provides a hydrophilic sidechain group that imparts aqueous solubility to the copolymer.

In some embodiments, the water-soluble carrier monomer within the polyacrylamide-based copolymer provides an inert barrier at an interface of an aqueous formulation to prevent protein-protein interactions. In some embodiments, the interface is an air-water interface. In some embodiments, the interface is an enclosure-water interface, including, but not limited to, a glass-water interface, a rubber-water interface, a plastic-water interface, or a metal-water interface. In some embodiments, the interface is an oil-water interface. In some embodiments, the interface is an interface between a liquid and tubing. In some embodiments, the interface is an interface between a liquid and a catheter. In some embodiments, the enclosure-water interface is in a pump system. In some embodiments, the enclosure-water interface is in a closed-loop system.

In some embodiments, the water-soluble carrier monomer is hydrophilic and/or nonionic. Examples of water-soluble carrier monomers of interest include, but are not limited to, acrylamide (AM), N-(3-methoxypropoyl)acrylamide (MPAM), 4-acryloylmorpholine (MORPH), N,N-dimethylacrylamide (DMA), and N-hydroxyethyl acrylamide (HEAM).

The term "functional dopant monomer," as used herein, refers to an acrylamide monomer species that has one or more physicochemical properties (e.g., hydrophobicity, charge, etc.) different from those of the water-soluble carrier monomer. In some embodiments, the functional dopant monomer within the polyacrylamide-based copolymer promotes association of the polymers to an interface of the composition; such interfaces can include, but are not limited to, polymer-air-water interface interactions, polymer-protein interactions, polymer-peptide interactions, polymer-micelle interactions, polymer-liposome interactions, and polymer-lipid nanoparticle interactions. The functional dopant monomer can act as a stabilizing moiety to facilitate interactions with biomolecules, for example, proteins, peptides, antibodies, antibody-drug conjugates, nucleic acids, lipid particles, and combinations thereof (e.g., to prevent aggregation of the biomolecules). The functional dopant monomers can be further classified into hydrogen-bonding, ionic, hydrophobic, and aromatic monomers based on their chemical composition. Typically, the functional dopant monomers are copolymerized at a lower weight percentage in the co-polymer as compared to the water-soluble carrier monomers.

The term "polymerization" refers to the process in which monomer molecules undergo a chemical reaction to form polymeric chains or three-dimensional networks. Different types of polymerization reactions are known in the art, for example, addition (chain-reaction) polymerization, condensation polymerization, ring-opening polymerization, free radical polymerization, controlled radical polymerization, atom transfer radical polymerization (ATRP), single-electron transfer living radical polymerization (SET-LRP), reversible addition-fragmentation chain transfer (RAFT) polymerization, nitroxide-mediated polymerization (NMP), and emulsion polymerization. The polymerization reaction can be a vinyl addition polymerization initiated via a free radical generating system. In some embodiments, the copolymers of the present disclosure are prepared using RAFT polymerization.

The term "degree of polymerization" (DP) refers to the number of monomer units in a polymer. It is calculated by dividing the average molecular weight of a polymer sample by the molecular weight of the monomers. The average molecular weight of a polymer can be represented by the number-averaged molecular weight (Mn), the weight-average molecular weight (Mw), the Z-average molecular weight (Mz) or the molecular weight at the peak maxima of the molecular weight distribution curve (Mp). The average molecular weight of a polymer can be determined by a variety of analytical characterization techniques known to those skilled in the art, for example, gel permeation chromatography (GPC), static light scattering (SLS) analysis, multi-angle laser light scattering (MALLS) analysis, nuclear magnetic resonance spectroscopy (NMR), intrinsic viscometry (IV), melt flow index (MFI), and matrix-assisted laser desorption/ionization mass spectrometry (MALDI-MS), and combinations thereof. Degree of polymerization can also be determined experimentally using suitable analytical methods known in the art, such as nuclear magnetic spectroscopy (NMR), Fourier Transform infrared spectroscopy (FT-IR) and Raman spectroscopy.

The compositions described herein can include a polyacrylamide-based copolymer composed of:
a water-soluble carrier monomer selected from N-(3-methoxypropyl)acrylamide (MPAM), 4-acryloylmorpholine (MORPH), N,N-dimethylacrylamide (DMA), N-hydroxyethyl acrylamide (HEAM), acrylamide (AM), and combinations thereof; and
a functional dopant monomer selected from N-[tris(hydroxymethyl)-methyl]acrylamide (TRI), 2-acrylamido-2-methylpropane sulfonic acid (AMP), (3-acrylamidopropyl)trimethylammonium chloride (TMA), N-isopropylacrylamide (NIP), N,N-diethylacrylamide (DEA), N-tert-butylacrylamide (TBA), N-phenylacrylamide (PHE), and combinations thereof.

In some embodiments, the water-soluble carrier monomer of the polyacrylamide-based copolymer is selected from MORPH, MPAM, and combinations thereof. In some embodiments, the water-soluble carrier monomer includes MORPH or MPAM. In some embodiments, the water-soluble carrier monomer is MORPH. In some embodiments, the water-soluble carrier monomer is MPAM.

In some embodiments, the functional dopant monomer of the polyacrylamide-based copolymer is selected from AMP, TMA, TBA, PHE, and combinations thereof. In some embodiments, the functional dopant monomer includes TRI, PHE, or NIP. In some embodiments, the functional dopant monomer includes DEA, PHE, or NIP. In some embodiments, the functional dopant monomer is NIP. In some embodiments, the functional dopant monomer is PHE. In some embodiments, the functional dopant monomer is DEA.

In some embodiments, the water-soluble carrier monomer is selected from MPAM, MORPH, and combinations thereof, and the functional dopant monomer is selected from NIP, PHE, and combinations thereof. In some embodiments, the water-soluble carrier monomer is selected from MPAM, MORPH, and combinations thereof, and the functional dopant monomer is selected from DEA, NIP, PHE, and combinations thereof. In some embodiments, the water-soluble carrier monomer is selected from MPAM, MORPH, and combinations thereof, and the functional dopant monomer is selected from AMP, TMA, TBA, PHE, and combinations thereof. In some embodiments, the water-soluble carrier monomer includes MPAM, and the functional dopant monomer includes PHE. In some embodiments, the water-soluble carrier monomer includes MORPH, and the functional dopant monomer includes PHE. In some embodiments, the water-soluble carrier monomer includes MORPH, and the functional dopant monomer includes NIP. In some embodiments, the water-soluble carrier monomer includes MORPH or MPAM, and the functional dopant monomer includes DEA.

In some embodiments, the copolymer contains about 70 wt % to about 98 wt % of the water-soluble carrier monomer, for example, about 70 wt % to about 95 wt %, about 70 wt % to about 90 wt %, about 75 wt % to about 98 wt %, 75 wt % to about 95 wt %, about 75 wt % to about 90 wt %, about 80 wt % to about 98 wt %, about 80 wt % to about 95 wt %, about 80 wt % to about 90 wt %, about 83 wt % to about 98 wt %, about 83 wt % to about 95 wt %, or about 83 wt % to about 90 wt % of the water-soluble carrier monomer. In some embodiments, the copolymer contains about 2 wt % to about 30 wt % of the functional dopant monomer, for example, about 2 wt % to about 20 wt %, about 2 wt % to about 17 wt %, about 5 wt % to about 30 wt %, about 5 wt % to about 20 wt %, about 5 wt % to about 17 wt %, about 10 wt % to about 30 wt %, about 10 wt % to about 20 wt %, or about 10 wt % to about 17 wt % of the functional dopant monomer.

In some embodiments, the copolymer contains 70 wt % to 98 wt % of the water-soluble carrier monomer, for example, 70 wt % to 95 wt %, 70 wt % to 90 wt %, 75 wt % to 98 wt %, 75 wt % to 95 wt %, 75 wt % to 90 wt %, 80 wt % to 98 wt %, 80 wt % to 95 wt %, 80 wt % to 90 wt %, 83 wt % to 98 wt %, 83 wt % to 95 wt %, or 83 wt % to 90 wt % of the water-soluble carrier monomer. In some embodiments, the copolymer contains 2 wt % to 30 wt % of the functional dopant monomer, for example, 2 wt % to 20 wt %, 2 wt % to 17 wt %, 5 wt % to 30 wt %, 5 wt % to 20 wt %, 5 wt % to 17 wt %, 10 wt % to 30 wt %, 10 wt % to 20 wt %, or 10 wt % to 17 wt % of the functional dopant monomer.

In some embodiments, the copolymer contains about 70 wt % to about 85 wt %, about 70 wt % to about 80 wt %, about 74 wt % to about 85 wt %, about 74 wt % to about 80 wt %, or about 77 wt % of MORPH. In some embodiments, the copolymer contains about 15 wt % to about 30 wt %, about 15 wt % to about 26 wt %, about 20 wt % to about 30 wt %, about 20 wt % to about 26 wt %, or about 23 wt % of NIP. In some embodiments, the copolymer contains 70 wt % to 85 wt %, 70 wt % to 80 wt %, 74 wt % to 85 wt %, 74 wt % to 80 wt %, or 77 wt % of MORPH. In some embodiments, the copolymer contains 15 wt % to 30 wt %, 15 wt % to 26 wt %, 20 wt % to 30 wt %, 20 wt % to 26 wt %, or 23 wt % of NIP.

In some embodiments, the copolymer contains about 80 wt % to about 99 wt %, about 85 wt % to about 98 wt %, about 88 wt % to about 96 wt %, about 90 wt % to about 95 wt %, or about 94 wt % of MORPH. In some embodiments, the copolymer contains about 2 wt % to about 15 wt %, about 4 wt % to about 15 wt %, about 4 wt % to about 10 wt %, about 5 wt % to about 10 wt %, or about 6 wt % of PHE. In some embodiments, the copolymer contains 80 wt % to 99 wt %, 85 wt % to 98 wt %, 88 wt % to 96 wt %, 90 wt % to 95 wt %, or 94 wt % of MORPH. In some embodiments, the copolymer contains 2 wt % to 15 wt %, 4 wt % to 15 wt %, 4 wt % to 10 wt %, 5 wt % to 10 wt %, or 6 wt % of PHE.

In some embodiments, the copolymer contains about 80 wt % to about 99 wt %, about 85 wt % to about 98 wt %, about 88 wt % to about 96 wt %, about 90 wt % to about 95 wt %, or about 92 wt % of MORPH. In some embodiments, the copolymer contains about 2 wt % to about 15 wt %, about 4 wt % to about 15 wt %, about 4 wt % to about 10 wt %, about 5 wt % to about 10 wt %, or about 8 wt % of PHE. In some embodiments, the copolymer contains 80 wt % to 99 wt %, 85 wt % to 98 wt %, 88 wt % to 96 wt %, 90 wt % to 95 wt %, or 92 wt % of MORPH. In some embodiments, the copolymer contains 2 wt % to 15 wt %, 4 wt % to 15 wt %, 4 wt % to 10 wt %, 5 wt % to 10 wt %, or 8 wt % of PHE.

In some embodiments, a degree of polymerization of the copolymer is about 10 to about 500, for example, about 10 to about 350, about 10 to about 200, about 15 to about 500, about 15 to about 350, about 15 to about 200, about 20 to about 500, about 20 to about 350, or about 20 to about 200.

In some embodiments, a degree of polymerization of the copolymer is 10 to 500, for example, 10 to 350, 10 to 200, 15 to 500, 15 to 350, 15 to 200, 20 to 500, 20 to 350, or 20 to 200.

In some embodiments, a number-average molecular weight of the copolymer is about 2,000 g/mol to about 10,000 g/mol, for example, about 2,000 g/mol to about 7,500 g/mol, 2,000 g/mol to about 6,000 g/mol, about 2,000 g/mol to about 5,000 g/mol, about 3,000 g/mol to about 10,000 g/mol, about 3,000 g/mol to about 7,500 g/mol, about 3,000 g/mol to about 6,000 g/mol, or about 3,000 g/mol to about 5,000 g/mol. In some embodiments, a number-average molecular weight of the copolymer is 2,000 g/mol to 10,000 g/mol, for example, 2,000 g/mol to 7,500 g/mol, 2,000 g/mol to 6,000 g/mol, 2,000 g/mol to 5,000 g/mol, 3,000 g/mol to 10,000 g/mol, 3,000 g/mol to 7,500 g/mol, 3,000 g/mol to 6,000 g/mol, or 3,000 g/mol to 5,000 g/mol.

In some embodiments, the composition includes about 0.1 wt % to about 10 wt % of the copolymer, for example, about 0.1 wt % to about 5 wt %, about 0.1 wt % to about 2.5 wt %, about 0.25 wt % to about 10 wt %, about 0.25 wt % to about 5 wt %, about 0.25 wt % to about 2.5 wt %, about 0.5 wt % to about 10 wt %, about 0.5 wt % to about 5 wt %, or about 2.5 wt % of the copolymer. In some embodiments, the composition includes about 1 wt % of the copolymer. In some embodiments, the composition includes 0.1 wt % to 10 wt % of the copolymer, for example, 0.1 wt % to 5 wt %, 0.1 wt % to 2.5 wt %, 0.25 wt % to 10 wt %, 0.25 wt % to 5 wt %, 0.25 wt % to 2.5 wt %, 0.5 wt % to 10 wt %, 0.5 wt % to 5 wt %, or 2.5 wt % of the copolymer. In some embodiments, the composition includes 1 wt % of the copolymer.

Antibodies

As summarized above, this disclosure provides compositions of antibodies formulated with a polyacrylamide-based copolymer. The inventors have demonstrated that polyacrylamide-based copolymers can be used to provide stable a formulation, such as an aqueous formulation, of a therapeutic antibody without altering its pharmacokinetics or bioavailability. This formulation can be applied to a variety of antibodies.

The term "antibody" is used herein in its broadest sense and includes certain types of immunoglobulin molecules comprising one or more antigen-binding domains that specifically bind to an antigen or epitope. An antibody specifically includes, but is not limited to, full length antibodies (e.g., intact immunoglobulins), antibody fragments, monoclonal antibodies, polyclonal antibodies, multispecific antibodies (e.g., bispecific antibodies), humanized fully human antibodies, chimeric antibodies, and single domain antibodies.

In some embodiments, the antibody is a monoclonal antibody. In some embodiments, the antibody is monospecific, i.e., binds a single antigen. In some embodiments, the monoclonal antibody is an IgG1 antibody, an IgG2 antibody, an IgG3 antibody, an IgG4 antibody, an IgM antibody, or any hybrid thereof.

In some embodiments, the antibody is a chimeric antibody. The term "chimeric antibody" refers to an antibody that contains one or more regions from one antibody and one or more regions from one or more other antibodies.

In some embodiments, the antibody is multispecific, i.e., binds multiple antigens, e.g., a bispecific antibody.

In some embodiments, the antibody is an antibody fragment. An "antibody fragment" includes a portion of an intact antibody, such as the antigen-binding or variable region of an intact antibody. Antibody fragments suitable for use in the present compositions include, for example, Fv fragments, Fab fragments, F(ab')$_2$ fragments, Fab' fragments, scFv (sFv) fragments, and scFv-Fc fragments.

In some embodiments, the antibody is a single domain antibody, e.g., a camelid antibody, or nanobody.

In some embodiments, the antibody is an antibody-drug conjugate, e.g., an antibody conjugated to one or more heterologous molecule(s). The heterologous molecule can be a small molecule (e.g., an organic compound with a molecular weight of less than 1000, 900, 800, 700, 600, or 500 Daltons). In some embodiments, the heterologous molecule is a cytotoxic agent, a chemotherapeutic agent, or a cytostatic agent.

In some embodiments, the antibody is a bispecific antibody immunoconjugate.

In some embodiments, the antibody is an antibody fragment. In some embodiments, the antibody includes one or more single-chain variable fragments (scFv) of a monoclonal antibody. In some embodiments, the monoclonal antibody is a humanized antibody, a human antibody, a murine antibody, or a chimeric (mouse/human) antibody.

The antibody can be targeted to a variety of target proteins, e.g., a therapeutic target protein.

In some embodiments, the antibody has a molecular weight of about 100 kDa to about 200 kDa, for example, about 120 kDa to about 180 kDa. In some embodiments, the antibody has a molecular weight of about 150 kDa. In some embodiments, the antibody has a molecular weight of 100 kDa to 200 kDa, for example, 120 kDa to 180 kDa. In some embodiments, the antibody has a molecular weight of 150 kDa. In some embodiments, the antibody has a molecular weight of 100 kDa or less, such as 40 kDa to 80 kDa, for example, about 50 kDa.

In some embodiments, the composition includes 5 wt % or more of the antibody, for example, 7.5 wt % or more, 10 wt % or more, 11 wt % or more, 12 wt % or more, 12.5 wt % or more, 15 wt % or more, 20 wt % or more, or 25 wt % or more of the antibody. In some embodiments, the composition includes 25 wt % or less, 20 wt % or less, or 15 wt % or less of the antibody.

In some embodiments, the composition includes about 2.5 wt % to about 25 wt % of the antibody, for example, about 2.5 wt % to about 20 wt %, about 2.5 wt % to about 15 wt %, or about 2.5 wt % to about 12.5 wt %, about 4 wt % to about 25 wt %, about 4 wt % to about 20 wt %, about 4 wt % to about 15 wt %, about 4 wt % to about 12.5 wt %, about 8 wt % to about 25 wt %, about 8 wt % to about 20 wt %, about 8 wt % to about 15 wt %, or about 8 wt % to about 12.5 wt % of the antibody. In some embodiments, the composition includes about 5.5 wt %, or about 12 wt % of the antibody. In some embodiments, the composition includes 2.5 wt % to 25 wt % of the antibody, for example, 2.5 wt % to 20 wt %, 2.5 wt % to 15 wt %, or 2.5 wt % to 12.5 wt %, 4 wt % to 25 wt %, 4 wt % to 20 wt %, 4 wt % to 15 wt %, 4 wt % to 12.5 wt %, 8 wt % to 25 wt %, 8 wt % to 20 wt %, 8 wt % to 15 wt %, or 8 wt % to 12.5 wt % of the antibody. In some embodiments, the composition includes about 5.5 wt % or about 12 wt % of the antibody, such as 5.5 wt % or 12 wt % of the antibody.

In some embodiments, 70% or more of the antibody, for example, 75 wt % or more, 80 wt % or more, 85 wt % or more, or 90 wt % or more of the antibody is present in the composition in a monomeric state.

Pharmaceutical Compositions

In some embodiments, the antibody composition including the acrylamide-based copolymer (e.g., as described above) is a pharmaceutical composition, and further includes a pharmaceutically acceptable excipient. The term "pharmaceutical composition" refers to a preparation which is in such form as to permit the biological activity of an active ingredient contained therein to be administered to, and effective in treating, a subject, and which contains no additional components which are unacceptably toxic to the subject.

The pharmaceutical composition may contain formulation materials for modifying, maintaining, or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids; antimicrobials; antioxidants; buffers; chelating agents; complexing agents; monosaccharides; disaccharides and other carbohydrates; emulsifying agents; salt-forming counterions; preservatives; solvents; sugar alcohols; suspending agents; surfactants or wetting agents; stability enhancing agents; tonicity enhancing agents; delivery vehicles; diluents; other excipients and/or pharmaceutical adjuvants. Neutral buffered saline or saline mixed with conspecific serum albumin are examples of appropriate diluents. In accordance with appropriate industry standards, preservatives may also be added. The composition may be formulated as a lyophilizate using appropriate excipient solutions as diluents. Suitable components are nontoxic to recipients at the dosages and concentrations employed. Further examples of components that may be employed in pharmaceutical formulations are presented in Remington's Pharmaceutical Sciences, 16th Ed. (1980) and 20th Ed. (2000), Mack Publishing Company, Easton, PA.

In some embodiments, the compositions described herein further include a surfactant. In some embodiments, the composition includes about 0.001 wt % to about 1 wt %, for example, about 0.001 wt % to about 0.5 wt %, about 0.001 wt % to about 0.1 wt %, about 0.001 wt % to about 0.05 wt %, about 0.005 wt % to about 0.5 wt %, about 0.005 wt % to about 0.1 wt %, about 0.005 wt % to about 0.05 wt %, about 0.01 wt % to about 0.5 wt %, about 0.01 wt % to about 0.1 wt %, or about 0.01 wt % to about 0.05 wt % of a surfactant. In some embodiments, the composition includes 0.001 wt % to 1 wt %, for example, 0.001 wt % to 0.5 wt %, 0.001 wt % to 0.1 wt %, 0.001 wt % to 0.05 wt %, 0.005 wt % to 0.5 wt %, 0.005 wt % to 0.1 wt %, 0.005 wt % to 0.05 wt %, 0.01 wt % to 0.5 wt %, 0.01 wt % to 0.1 wt %, or 0.01 wt % to 0.05 wt % of a surfactant. In some embodiments, the surfactant includes a poloxamer. In some embodiments, the surfactant includes a polysorbate. In some embodiments, the polysorbate is polysorbate 80 or polysorbate 20. In some embodiments, the composition includes about 0.01 wt % of polysorbate 80. In some embodiments, the composition includes about 0.01 wt % of polysorbate 80, such as 0.01 wt % of polysorbate 80.

In some embodiments, the compositions described herein further include a stabilizer. In some embodiments, the stabilizer includes a sugar. In some embodiments, the sugar is sucrose or trehalose. In some embodiments, the composition includes about 0.1 wt % to about 25 wt %, for example, about 0.1 wt % to about 15 wt %, about 0.1 wt % to about 12.5 wt %, about 2 wt % to about 25 wt %, about 2 wt % to about 15 wt %, about 2 wt % to about 12.5 wt %, about 5 wt % to about 25 wt %, about 5 wt % to about 15 wt %, or about 5 wt % to about 12.5 wt % of the stabilizer. In some embodiments, the composition includes 0.1 wt % to 25 wt %, for example, 0.1 wt % to 15 wt %, 0.1 wt % to 12.5 wt %, 2 wt % to 25 wt %, 2 wt % to 15 wt %, 2 wt % to 12.5 wt %, 5 wt % to 25 wt %, 5 wt % to 15 wt %, or 5 wt % to 12.5 wt % of the stabilizer. In some embodiments, the composition includes about 9 wt % of sucrose. In some embodiments, the composition includes about 9 wt % of sucrose, such as 9 wt % of sucrose.

In some embodiments, the compositions described herein further include a buffer. In some embodiments, the composition has a buffer concentration of about 1 mM to about 100 mM, for example, about 1 mM to about 75 mM, about 1 mM to about 50 mM, about 5 mM to about 100 mM, about 5 mM to about 75 mM, about 5 mM to about 50 mM, about 10 mM to about 100 mM, about 10 mM to about 75 mM, or about 10 mM to about 50 mM. In some embodiments, the composition has a buffer concentration of 1 mM to 100 mM, for example, 1 mM to 75 mM, 1 mM to 50 mM, 5 mM to 100 mM, 5 mM to 75 mM, 5 mM to 50 mM, 10 mM to 100 mM, 10 mM to 75 mM, or 10 mM to 50 mM. In some embodiments, the buffer includes phosphate, citrate, acetate, TRIS, succinate, other organic acids, or histidine. In some embodiments, the buffer includes one or more phosphate salts. In some embodiments, the buffer includes sodium phosphate. In some embodiments, the composition includes an acetate buffer.

In some embodiments, the composition is an aqueous formulation. In certain embodiments, such aqueous formulations have a pH of 3 to 7.5, such as a pH of 4 to 6.5.

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the polypeptide. For example, suitable compositions may be water for injection, physiological saline solution for parenteral administration.

In some embodiments, the pharmaceutical composition is formulated for intravenous, intramuscular, or subcutaneous administration. For intravenous, cutaneous or subcutaneous injection, or injection at the site of affliction, the active ingredient will be in the form of a parenterally acceptable aqueous formulation, such as a solution, which is pyrogen-free and has suitable pH, isotonicity, and stability. Those of relevant skill in the art are well able to prepare suitable aqueous formulations using, for example, isotonic vehicles such as Sodium Chloride Injection, Ringer's Injection, Lactated Ringer's Injection. Preservatives, stabilizers, buffers, antioxidants and/or other additives can be included, as required.

Methods

Aspects of this disclosure include methods of using the compositions that include administering an antibody composition (e.g., as described herein) to a subject in need thereof. In some embodiments, administration is via intravenous injection. In some embodiments, administration is via subcutaneous injection. In some embodiments, the composition administered includes a therapeutically effective amount of a therapeutic antibody of interest.

Definitions

As used herein, the term "subject" means a mammalian subject. Exemplary subjects include humans, monkeys, apes, dogs, cats, mice, rats, cows, horses, camels, goats, rabbits, and sheep. In certain embodiments, the subject is a human.

In some embodiments the subject has a disease or condition that can be treated with an antibody as described herein. The term "treating" (and variations thereof such as "treat" or "treatment") refers to clinical intervention in an attempt to alter the natural course of a disease or condition in a subject in need thereof. Treatment can be performed during the course of clinical pathology. Desirable effects of treatment can include one or more of reducing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

The term "therapeutically effective amount" or "effective amount" refers to an amount of an antibody or pharmaceutical composition that, when administered to a subject, is effective to treat a disease or disorder. The exact dose or amount will depend on the purpose of the treatment and will typically be ascertainable by one skilled in the art using known techniques (see, e.g., Lloyd (1999) The Art, Science and Technology of Pharmaceutical Compounding).

As used herein, the terms "a," "an," and "the" include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (for example, 1%, 2%, 3%, and 4%) and the sub-ranges (for example, 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

As used herein, the term "about" can allow for a degree of variability in a value or range that is within 5% of a stated value or of a stated limit of a range.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

Unless otherwise defined herein, scientific and technical terms used in the present disclosure shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques disclosed herein are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, PA. Briefly, each heavy chain typically comprises a heavy chain variable region ($V_H$) and a heavy chain constant region ($C_H$). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antigen-binding protein" (ABP) refers to a protein comprising one or more antigen-binding domains that specifically bind to an antigen or epitope. In some embodiments, the antigen-binding domain binds the antigen or epitope with specificity and affinity similar to that of naturally occurring antibodies. In some embodiments, the ABP comprises an antibody. In some embodiments, the ABP comprises an antibody fragment.

The term "antigen-binding domain" means the portion of an ABP that is capable of specifically binding to an antigen or epitope.

The terms "full length antibody," "intact antibody," and "whole antibody" are used herein interchangeably to refer to an antibody having a structure substantially similar to a naturally occurring antibody structure and having heavy chains that comprise an Fc region.

The term "Fc region" means the C-terminal region of an immunoglobulin heavy chain that, in naturally occurring antibodies, interacts with Fc receptors and certain proteins of the complement system. The structures of the Fc regions of various immunoglobulins, and the glycosylation sites contained therein, are known in the art. See Schroeder and Cavacini, *J. Allergy Clin. Immunol.*, 2010, 125:S41-52, incorporated by reference in its entirety. The Fc region may be a naturally occurring Fc region, or an Fc region modified as described elsewhere in this disclosure.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., *Sequences of Proteins of Immunological Interest* 5th ed. (1991) Public Health Service, National Institutes of Health, Bethesda, MD, incorporated by reference in its entirety.

The light chain from any vertebrate species can be assigned to one of two types, called kappa (κ) and lambda (λ), based on the sequence of its constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme); each of which is incorporated by reference in its entirety.

Table 1 provides the positions of CDR1-L (CDR1 of $V_L$), CDR2-L (CDR2 of $V_L$), CDR3-L (CDR3 of $V_L$), CDR1-H (CDR1 of $V_H$), CDR2-H (CDR2 of $V_H$), and CDR3-H (CDR3 of $V_H$), as identified by the Kabat and Chothia schemes. For CDR1-H, residue numbering is provided using both the Kabat and Chothia numbering schemes.

CDRs may be assigned, for example, using antibody numbering software, such as Abnum, available at www.bioinf.org.uk/abs/abnum/, and described in Abhinandan and Martin, *Immunology*, 2008, 45:3832-3839, incorporated by reference in its entirety.

TABLE 1

Residues in CDRs according to Kabat and Chothia numbering schemes.

| CDR | Kabat | Chothia |
|---|---|---|
| CDR1-L | 24-34 | 24-34 |
| CDR2-L | 50-56 | 50-56 |
| CDR3-L | 89-97 | 89-97 |
| CDR1-H (Kabat Numbering) | 31-35B | 26-32 or 34* |
| CDR1-H (Chothia Numbering) | 31-35 | 26-32 |
| CDR2-H | 50-65 | 52-56 |
| CDR3-H | 95-102 | 95-102 |

*The C-terminus of CDR1-H, when numbered using the Kabat numbering convention, varies between 32 and 34, depending on the length of the CDR.

The "EU numbering scheme" is generally used when referring to a residue in an antibody heavy chain constant region (e.g., as reported in Kabat et al., supra).

An "antibody fragment" comprises a portion of an intact antibody, such as the antigen-binding or variable region of an intact antibody. Antibody fragments include, for example, Fv fragments, Fab fragments, F(ab')2 fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by recombinant methods or by papain digestion of a full-length antibody.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). In some embodiments, the linker is a (GGGGS)$_n$. In some embodiments, n=1, 2, 3, 4, 5, or 6. See Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain comprises an IgG4 Fc domain.

The term "single domain antibody" refers to a molecule in which one variable domain of an antibody specifically binds to an antigen without the presence of the other variable domain. Single domain antibodies, and fragments thereof, are described in Arabi Ghahroudi et al., *FEBS Letters*, 1998, 414:521-526 and Muyldermans et al., *Trends in Biochem. Sci.*, 2001, 26:230-245, each of which is incorporated by reference in its entirety.

A "monospecific ABP" is an ABP that comprises a binding site that specifically binds to a single epitope. An example of a monospecific ABP is a naturally occurring IgG molecule which, while divalent, recognizes the same epitope at each antigen-binding domain. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature*, 1986, 321:522-525; Riechmann et al., *Nature*, 1988, 332:323-329; and Presta, *Curr. Op. Struct. Biol.*, 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies. In some embodiments, rodents are genetically engineered to replace their rodent antibody sequences with human antibodies.

An "immunoconjugate" is an ABP conjugated to one or more heterologous molecule(s). In some embodiments, the immunoconjugate is an antibody conjugated to one or more heterologous molecule(s), i.e., an antibody-drug conjugate. The heterologous molecule can be a small molecule. In some embodiments, the heterologous molecule is a cytotoxic agent, a chemotherapeutic agent or a cytostatic agent.

The term "cytotoxic agent," as used herein, refers to a substance that inhibits or prevents a cellular function and/or causes cell death or destruction.

A "chemotherapeutic agent" refers to a chemical compound useful in the treatment of cancer. Chemotherapeutic agents include "anti-hormonal agents" or "endocrine therapeutics" which act to regulate, reduce, block, or inhibit the effects of hormones that can promote the growth of cancer.

The term "cytostatic agent" refers to a compound or composition which arrests growth of a cell either in vitro or in vivo. In some embodiments, a cytostatic agent is an agent that reduces the percentage of cells in S phase. In some embodiments, a cytostatic agent reduces the percentage of cells in S phase by at least about 20%, at least about 40%, at least about 60%, or at least about 80%.

The term "tumor" refers to all neoplastic cell growth and proliferation, whether malignant or benign, and all precancerous and cancerous cells and tissues. The terms "cancer," "cancerous," "cell proliferative disorder," "proliferative disorder" and "tumor" are not mutually exclusive as referred to herein. The terms "cell proliferative disorder" and "proliferative disorder" refer to disorders that are associated with some degree of abnormal cell proliferation. In some embodiments, the cell proliferative disorder is a cancer.

A "variant" of a polypeptide (e.g., an antibody) comprises an amino acid sequence wherein one or more amino acid residues are inserted into, deleted from and/or substituted into the amino acid sequence relative to the native polypeptide sequence, and retains essentially the same biological activity as the native polypeptide. The biological activity of the polypeptide can be measured using standard techniques in the art (for example, if the variant is an antibody, its activity may be tested by binding assays, as described herein). Variants of the present disclosure include fragments, analogs, recombinant polypeptides, synthetic polypeptides, and/or fusion proteins.

A "derivative" of a polypeptide is a polypeptide (e.g., an antibody) that has been chemically modified, e.g., via conjugation to another chemical moiety such as, for example, polyethylene glycol, albumin (e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

"Affinity" refers to the strength of the sum total of non-covalent interactions between a single binding site of a molecule (e.g., an ABP) and its binding partner (e.g., an antigen or epitope). Unless indicated otherwise, as used herein, "affinity" refers to intrinsic binding affinity, which reflects a 1:1 interaction between members of a binding pair (e.g., ABP and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein. Affinity can be determined, for example, using surface plasmon resonance (SPR) technology (e.g., BIACORE®) or biolayer interferometry (e.g., FORTEBIO®).

With regard to the binding of an ABP to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the ABP to the target molecule is competitively inhibited by the control molecule.

The term "polymer" refers to a substance or material consisting of repeating monomer subunits. The term "copolymer" refers to a polymer composed of two or more distinct repeating monomer subunits.

Additional Embodiments

The disclosure is further described by the following non-limiting clauses:

Clause 1. A composition comprising: a polyacrylamide-based copolymer comprising: a water-soluble carrier monomer selected from N-(3-methoxypropyl)acrylamide (MPAM), 4-acryloylmorpholine (MORPH), N,N-dimethylacrylamide (DMA), N-hydroxyethyl acrylamide (HEAM), acrylamide (AM), and combinations thereof; and a functional dopant monomer selected from N-[tris(hydroxymethyl)-methyl]acrylamide (TRI), 2-acrylamido-2-methylpropane sulfonic acid (AMP), (3-acrylamidopropyl)trimethylammonium chloride (TMA), N-isopropylacrylamide (NIP), N—N-diethylacrylamide (DEA), N-tert-butylacrylamide (TBA), N-phenylacrylamide (PHE), and combinations thereof; and an antibody.

Clause 2. The composition of clause 1, wherein the water-soluble carrier monomer is selected from MORPH, MPAM, and combinations thereof.

Clause 3. The composition of clause 1, wherein the water-soluble carrier monomer comprises MORPH.

Clause 4. The composition of clause 1, wherein the water-soluble carrier monomer comprises MPAM.

Clause 5. The composition of any one of clauses 1-4, wherein the functional dopant monomer is selected from AMP, TMA, TBA, PHE, and combinations thereof.

Clause 6. The composition of any one of clauses 1-4, wherein the functional dopant monomer is selected from DEA, PHE, NIP, and combinations thereof.

Clause 7. The composition of any one of clauses 1-4, wherein the functional dopant monomer comprises TRI.

Clause 8. The composition of any one of clauses 1-4, wherein the functional dopant monomer comprises PHE.

Clause 9. The composition of any one of clauses 1-4, wherein the functional dopant monomer comprises NIP.

Clause 10. The composition of any one of clauses 1-4, wherein the functional dopant monomer comprises DEA.

Clause 11. The composition of clause 1, wherein: the water-soluble carrier monomer is selected from MPAM, MORPH, and combinations thereof; and the functional dopant monomer is selected from NIP, PHE, and combinations thereof.

Clause 12. The composition of clause 1, wherein: the water-soluble carrier monomer is selected from MPAM, MORPH, and combinations thereof; and the functional dopant monomer is selected from AMP, TMA, TBA, PHE, and combinations thereof.

Clause 13. The composition of clause 1, wherein the water-soluble carrier monomer is MPAM, and the functional dopant monomer is PHE.

Clause 14. The composition of clause 1, wherein the water-soluble carrier monomer is MORPH, and the functional dopant monomer is PHE.

Clause 15. The composition of clause 1, wherein the water-soluble carrier monomer is MORPH, and the functional dopant monomer is NIP.

Clause 16. The composition of any one of clauses 1-15, wherein the copolymer comprises: 70 wt % to 98 wt % of the water-soluble carrier monomer; and 2 wt % to 30 wt % of the functional dopant monomer.

Clause 17. The composition of any one of clauses 1-15, wherein the copolymer comprises: 80 wt % to 95 wt % of the water-soluble carrier monomer; and 5 wt % to 20 wt % of the functional dopant monomer.

Clause 18. The composition of any one of clauses 1-15, wherein the copolymer comprises: 83 wt % to 98 wt % of the water-soluble carrier monomer; and 2 wt % to 17 wt % of the functional dopant monomer.

Clause 19. The composition of clause 1, wherein the copolymer comprises: 70 wt % to 85 wt % of MORPH; and 15 wt % to 30 wt % of NIP.

Clause 20. The composition of clause 1, wherein the copolymer comprises: 74 wt % to 80 wt % of MORPH; and 20 wt % to 26 wt % of NIP.

Clause 21. The composition of clause 1, wherein the copolymer comprises: 77 wt % of MORPH; and 23 wt % of NIP.

Clause 22. The composition of any one of clauses 1-21, wherein a degree of polymerization of the copolymer is 10 to 500.

Clause 23. The composition of any one of clauses 1-21, wherein a degree of polymerization of the copolymer is 20 to 200.

Clause 24. The composition of any one of clauses 1-23, wherein a number-average molecular weight of the copolymer is 2,000 g/mol to 10,000 g/mol.

Clause 25. The composition of any one of clauses 1-23, wherein a number-average molecular weight of the copolymer is 2,000 g/mol to 6,000 g/mol.

Clause 26. The composition of any one of clauses 1-23, wherein a number-average molecular weight of the copolymer is 3,000 g/mol to 5,000 g/mol.

Clause 27. The composition of any one of clauses 1-26 comprising 0.1 wt % to 10 wt % of the copolymer.

Clause 28. The composition of any one of clauses 1-26, comprising 0.5 wt % to 5 wt % of the copolymer.

Clause 29. The composition of any one of clauses 1-28, comprising 1 wt % of the copolymer.

Clause 30. The composition of any one of clauses 1-29, wherein the composition further comprises a surfactant.

Clause 31. The composition of clause 30, comprising 0.001 wt % to 0.5 wt % of the surfactant.

Clause 32. The composition of clause 30, comprising 0.005 wt % to 0.05 wt % of the surfactant.

Clause 33. The composition of any one of clauses 30-32, wherein the surfactant comprises a polysorbate.

Clause 34. The composition of clause 33, wherein the polysorbate is polysorbate 80.

Clause 35. The composition of clause 34, comprising 0.005 wt % to 0.05 wt % of polysorbate 80.

Clause 36. The composition of clause 34, comprising 0.01 wt % of polysorbate 80.

Clause 37. The composition of any one of clauses 1-36, wherein the composition further comprises a stabilizer.

Clause 38. The composition of clause 37, comprising 0.1 wt % to 25 wt % of the stabilizer.

Clause 39. The composition of clause 38, comprising 2 wt % to 15 wt % of the stabilizer.

Clause 40. The composition of any one of clauses 37-39, wherein the stabilizer comprises an oligosaccharide.

Clause 41. The composition of clause 40, wherein the oligosaccharide is sucrose.

Clause 42. The composition of clause 40, comprising 2 wt % to 15 wt % of sucrose.

Clause 43. The composition of clause 40, comprising 9 wt % of sucrose.

Clause 44. The composition of any one of clauses 1-43, comprising 5 wt % or more of the antibody.

Clause 45. The composition of clause 44, comprising 10 wt % or more of the antibody.

Clause 46. The composition of clause 44 or 45, comprising 20 wt % or less of the antibody.

Clause 47. The composition of any one of clauses 1-43, comprising 2.5 wt % to 20 wt % of the antibody.

Clause 48. The composition of clause 47, comprising 2.5 wt % to 15 wt % of the antibody.

Clause 49. The composition of clause 47, comprising 8 wt % to 20 wt % of the antibody.

Clause 50. The composition of clause 49, comprising 12 wt % to 20 wt % of the antibody.

Clause 51. The composition of any one of clauses 1-50, wherein the antibody has a molecular weight of 100 kDa to 200 kDa.

Clause 52. The composition of clause 51, wherein the antibody has a molecular weight of 120 kDa to 180 kDa.

Clause 53. The composition of any one of clauses 1-50, wherein the antibody has a molecular weight of 50 kDa to 100 kDa.

Clause 54. The composition of any one of clauses 1-53, wherein the antibody is a monoclonal antibody.

Clause 55. The composition of any one of clauses 1-53, wherein the antibody is a chimeric antibody.

Clause 56. The composition of any one of clauses 1-53, wherein the antibody is a bispecific antibody.

Clause 57. The composition of any one of clauses 1-53, wherein the antibody is a full-length antibody.

Clause 58. The composition of any one of clauses 1-53, wherein the antibody is an antibody fragment.

Clause 59. The composition of any one of clauses 1-53, wherein the antibody is an antibody-drug conjugate.

Clause 60. The composition of clause 1, comprising: 0.1 wt % to 10 wt % of a polyacrylamide-based copolymer comprising: 70 wt % to 98 wt % of a water-soluble carrier monomer selected from MPAM, MORPH, DMA, HEAM, AM, and combinations thereof; and 2 wt % to 30 wt % of a functional dopant monomer selected from TRI, AMP, TMA, NIP, TBA, PHE, and combinations thereof; and 5 wt % or more of the antibody.

Clause 61. The composition of clause 60, comprising 10 wt % or more (e.g., 12 wt % to 20 wt %, such as 12 wt %) of the antibody.

Clause 62. The composition of clause 60 or 61, wherein: the water-soluble carrier monomer is selected from MPAM, MORPH, and combinations thereof; and the functional dopant monomer is selected from NIP, PHE, and combinations thereof.

Clause 63. The composition of any one of clauses 60-62, wherein: the water-soluble carrier monomer is MORPH; and the functional dopant monomer is NIP.

Clause 64. The composition of clause 63, wherein the composition comprises: 77 wt % of MORPH; and 23 wt % of NIP.

Clause 65. The composition of any one of clauses 60-64, comprising 1 wt % of the polyacrylamide-based copolymer.

Clause 66. The composition of any one of clauses 60-65, further comprising 0.001 wt % to 0.5 wt % of a surfactant.

Clause 67. The composition of any one of clauses 63-66, further comprising 0.1 wt % to 25 wt % of a stabilizer.

Clause 68. The composition of any one of clauses 1-67, wherein the composition is aqueous.

Clause 69. The composition of clause 68, wherein the composition has a pH of 3 to 7.5.

Clause 70. The composition of clause 69, wherein the composition has a pH of 4 to 6.5.

Clause 71. The composition of clause 69 or 70, further comprising: 0.001 wt % to 0.5 wt % of a surfactant (e.g., 0.01 wt % of polysorbate 80); 0.1 wt % to 25 wt % of a stabilizer (e.g., 9 wt % of sucrose); and a buffer (e.g., 20 mM acetate buffer).

Clause 72. The composition of any one of clauses 1-71, wherein at least 70% of the antibody is present in the composition in a monomeric state.

Clause 73. The composition of clause 72, wherein at least 90% of the antibody is present in the composition in a monomeric state.

Clause 74. The composition of any one of clauses 1-73, wherein the composition is a liquid having a surface tension of 60 mN/m or less.

Clause 75. The composition of any one of clauses 1-74, wherein the composition has an interfacial complex viscosity of 0.2 Pa·s·m or less.

Clause 76. The composition of any one of clauses 1-75, wherein the composition has a viscosity of 6 mPa·s or less at shear rates of 0 $s^{-1}$ to 3,000 $s^{-1}$.

Clause 77. The composition of any one of clauses 1-76, wherein the composition is capable of retaining 70% or more of a binding activity of the antibody for a target antigen over 21 days of continuous stressed aging, based upon half maximal inhibitory concentration as determined by an enzyme-linked immunosorbent assay.

Clause 78. The composition of any one of clauses 1-77, wherein the composition is formulated for subcutaneous administration.

Clause 79. The composition of any one of clauses 1-77, wherein the composition comprises a suspension of particles in a liquid carrier.

Clause 80. The composition of clause 79, wherein the liquid carrier is non-aqueous.

Clause 81. The composition of clause 79 or 80, wherein the particles comprise the polyacrylamide-based copolymer and the antibody.

Clause 82. A method of administering an antibody to a subject in need thereof, comprising injecting the subject with a therapeutically effective amount of a composition according to any one of clauses 1-81.

Clause 83. The method of clause 82, wherein the injection is subcutaneous.

Clause 84. A composition according to any one of clauses 1-81 for use in subcutaneous administration of an antibody to a subject.

Clause 85. Use of a composition according to any one of clauses 1-81 for the manufacture of a medicament for use in subcutaneous administration of an antibody to a subject.

EXAMPLES

Aspects of the disclosure may be further understood in light of the following examples, which should not be construed as limiting the scope of the disclosure in any way.

GENERAL EXPERIMENTAL DETAILS

Materials: Solvents N,N-dimethylformamide (DMF; >99.7%; HPLC grade, Alfa Aeser), ethanol (EtOH; >99.5%; Certified ACS, Acros Organics), acetone (>99.9%; Sigma-Aldrich, HPLC Grade), hexanes (>99.9%; Thermo Fisher Scientific, Certified ACS), ether (anhydrous, >99%; Sigma-Aldrich, Certified ACS), and $CDCl_3$ (>99.8%; Acros Organics) were used as received. MORPH (>97%; Sigma-Aldrich) was filtered with basic alumina before use. NIP (>99%; Sigma-Aldrich) was used as received. RAFT CTA 2-cyano-2-propyl dodecyl trithiocarbonate (2-CPDT; >97%; Strem Chemicals) was used as received. Initiator 2,2-azobis(2-methyl-propionitrile) (AIBN; >98%; Sigma-Aldrich) was recrystallized from MeOH (>99.9%; Thermo Fisher Scientific, HPLC grade) and dried under vacuum before use. Z group removing agents lauroyl peroxide (LPO; 97%; Sigma-Aldrich) and hydrogen peroxide ($H_2O_2$; 30%; Sigma-Aldrich) were used as received. PGT121 monoclonal antibody was provided by Just-Evotec Biologics, Inc. (Seattle, WA, USA) in collaboration with the Bill and Melinda Gates Foundation. PGT121 was supplied at 55.5 mg/mL in 20 mM acetate buffer with 9% (w/v) sucrose, 0.01% PS 80, pH 5.0. 9e9 anti-idiotype monoclonal antibody was synthesized by the Protein Production Facility (PPF) funded by the Bill and Melinda Gates Foundation, using a plasmid provided by the Vaccine Research Center (VIRC), a division of the National Institute of Allergy and Infectious Diseases (NIAID) in the US National Institutes of Health (NIH).

Synthesis of MoNi: The amphiphilic acrylamide copolymer excipient acryloylmorpholine$_{77\%}$-N-isopropylacrylamide$_{23\%}$ (MoNi 77:23) was prepared according to methods described by Mann et al., *Sci. Transl. Med.* 12, eaba6676 (2020). Briefly, MORPH (645 mg, 4.57 mmol, 41.5 eq.), NIP (105 mg, 0.93 mmol, 8.5 eq.), 2-CPDT (38 mg, 0.11 mmol, 1 eq.), and AIBN (3.6 mg, 0.02 mmol, 0.2 eq.) were combined and diluted with DMF to a total volume of 2.25 mL [33.3 (w/v) vinyl monomer concentration] in an 8-mL scintillation vial equipped with a PTFE septa. The reaction mixture was sparged with nitrogen gas for 10 min and then heated for 12 hours at 65° C. To remove the Z terminus of the resulting polymer, AIBN (360 mg, 2.2 mmol, 20 eq.) and LPO (88 mg, 0.22 mmol, 2 eq.) were added to the reaction mixture, which was then sparged with nitrogen gas for 10 min and heated for 12 hours at 90° C. Z group removal was confirmed by the ratio of the refractive index to ultraviolet (310 nm) intensity in SEC analysis. Resulting polymers were precipitated three times from ether and dried under vacuum overnight. Resulting composition and molecular weights were determined via $^1$H NMR spectroscopy and SEC with PEG standards.

Copolymer molecular weight characterization by SEC: $M_n$, $M_w$, and Đ for MoNi was determined via SEC implementing PEG standards (American Polymer Standards Corporation) after passing through two SEC columns [inner diameter, 7.8 mm; Mw range, 200 to 600,000 g mol$^{-1}$; Resolve Mixed Bed Low divinylbenzene (DVB) (Jordi Labs)] in a mobile phase of DMF with 0.1 M LiBr at 35° C. and a flow rate of 1.0 mL min$^{-1}$ [Dionex UltiMate 3000 pump, degasser, and autosampler (Thermo Fisher Scientific)].

Preparation of high-concentration, stabilized PGT121 formulations: PGT121 monoclonal antibody was concentrated via spin filtration (Corning® SpinX® UF 5 kDa MWCO) at 3030 RPM until desired volume recovery. Concentrated formulations were refrigerated for 12 hours before usage in accelerated aging studies.

Dynamic Light Scattering: DLS measurements of MoNi, prepared in MilliQ water, were taken on a DynaPro Plate Reader II, Wyatt Technology. Average of 5 acquisitions was reported.

Concentration determination: Concentrations of PGT121 formulations were determined by either volume recovery, ELISA, Nanodrop (Thermo Scientific) or aqueous SEC-UV (PBS buffer, 300 ppm sodium azide), depending on the assay. For aqueous SEC-UV, PGT121 aliquots were diluted 133× in MilliQ water and concentration was determined by comparing the area under the curve of the traces obtained from SEC using a Dionex UltiMate 3000 VWD at 280 nm (Thermo Scientific). In these assays, the aged sample was compared to an unaged 55 mg/mL PGT121 solution (n=3). For nanodrop, the protein concentration was compared to a stock standard at 55 mg/mL. For ELISA, concentrations were interpolated by fitting a four-parameter dose-response curve (variable slope) in GraphPad Prism 9. The high-concentration PGT121 formulation was reported as the mean±standard deviation of the concentration determined by these methods for several preparations of these formulations.

Surface Tension: Time-resolved surface tension of the air-solution interface was measured with a platinum/iridium Wilhelmy plate connected to an electrobalance (KSV Nima, Finland). The Wilhelmy plate was partially immersed in the aqueous solution in a Petri dish, and the surface tension of the interface was recorded for 50 min from the formation of a fresh interface. Equilibrium surface tension values (t=50 min) were reported as these values more closely describe the environment in a stored vial prior to agitation. Samples were diluted in 20 mM acetate buffer, pH=5.0, from stock samples to the desired assay concentrations. The experiment was repeated in triplicate.

Interfacial Rheology: Interfacial shear rheology was measured using a Discovery HR-3 rheometer (TA Instruments) with an interfacial geometry comprising a Du Noüy ring made of platinum/iridium wires (CSC Scientific, Fairfax, VA, catalog no. 70542000). Before each experiment, the Du Noüy ring was rinsed with ethanol and water and flame treated to remove organic contaminants. The solution chamber consisted of a double-wall Couette flow cell with an internal Teflon cylinder and an external glass beaker. A time sweep was performed at a strain of 1% (within the linear regime) and a frequency of 0.05 Hz (sufficiently low such that the effects due to instrument inertia will not be significant). Interfacial complex shear viscosity was measured for 30 min. Samples were diluted in 20 mM acetate buffer, pH=5.0, from stock samples to the desired assay concentrations. The experiment was repeated in triplicate.

PGT121 ELISA: The capture antibody, 9e9, was coated at 2 μg/mL in phosphate buffered saline (PBS) (25 μg per well) on Corning 96-well high binding flat-bottom half-area microplates (Fisher Scientific) and incubated at 4° C. overnight. The blocking buffer used was 2% non-fat dry milk (NFDM) in PBS, the assay buffer used was 2% bovine serum albumin (BSA) in PBS, and the wash buffer was PBS-T (0.05% Tween 20). Plates were washed twice and blocked with 125 μL of blocking buffer and incubated for 1 hr at room temperature. Sample dilutions and PGT121 standards were prepared in assay buffer. After blocking, assay buffer was removed from the plate before adding 50 μL of each sample and incubating for 1 hr at room temperature. Plates were washed five times before adding 50 μL per well of the secondary antibody, Peroxidase AffiniPure F(ab')$_2$ Fragment Goat Anti-Human IgG, Fcγ fragment specific (Jackson Immunoresearch, 109-036-008, RRID: AB\_2337591) was diluted 1:5000 in assay buffer. After incubating for 1 hr at room temperature, plates were washed 10 times and then developed by adding 50 μL of TMB ELISA Substrate (High Sensitivity) (Abcam, ab171523). Development was stopped after 2.5 min by adding 1 N hydrochloric acid. PGT121 concentration was measured by absorbance intensity at 450 nm using a Synergy H1 Hybrid Multi-Mode Plate Reader (BioTek). Each plate contained a 15-point standard curve assayed in duplicate which was used to interpolate PGT121 concentrations by fitting a four-parameter dose-response curve (variable slope) in GraphPad Prism 9. Stressed aging samples were diluted 1:10000 and then serially diluted by 4× to create a 7-point curve assayed in duplicate for each sample. IC$_{50}$ values were determined by fitting a four-parameter dose-response curve (variable slope) in GraphPad Prism 9. Mean value and standard deviation were reported.

In vivo pharmacokinetic study: Animal studies were conducted in accordance with the guidelines for care and use of laboratory animals under protocols approved by the Stanford Institutional Animal Care and Use Committee (IACUC). Eight week old female B6.Cg-Fcgrt$^{tm1Dcr}$ Prkdc$^{scid}$ Tg(FCGRT)32Dcr/DcrJ (The Jackson Laboratory, Stock No. 018441) mice were administered PGT121 antibody (1.5 mg/mouse) via IP or SC injection under brief isoflurane anesthesia (n=6/group). The polymer-stabilized high-concentration SC formulation was prepared with 102 mg/mL PGT121 (as determined by ELISA) and 1 wt % MoNi (15 μL injection volume), and the low concentration IP formulation was prepared at 5 mg/mL (300 μL injection volume) in the same buffer in which the antibody was provided. Blood samples were collected at 24 hours, 48 hours, and then at days 4, 7, 10, 14, and 21 post-injection for analysis of PGT121 serum concentration via ELISA.

Viscometry: A Rheosense m-VROC viscometer with a low viscosity chip was used to measure the viscosity at high shear rates representative of injection. Samples were measured from low to high shear rates using a Hamilton syringe. Each data point was collected at steady state.

In vitro stability assay: 150 μL of a PGT121 solution was diluted with 7.5 μL of MoNi in the formulation buffer at 21 mg/mL to reach a final excipient concentration of 0.1 wt. %. These formulations were agitated at 200 rpm at 50° C. 5 mL aliquots were removed every 24 hours.

Diffusion-Ordered Spectroscopy: $^1$H two-dimensional DOSY spectra were recorded at a PGT121 concentration of 0.2 mg/mL diluted from 20 mM acetate buffer with 9% (w/v) sucrose, 0.01% PS 80, pH 5.0 in $D_2O$ (Acros Organics) and dialyzed with 2000 Da MWCO Slide-A-Lyzer dialysis cassettes (Thermo Scientific) against $D_2O$ for 24 hours prior to use. MoNi was prepared directly in $D_2O$ at 0.1 mg/mL.

A Varian Inova 600 MHz NMR instrument was used to acquire the data. Magnetic field strengths ranging from 2 to 57 G cm$^{-1}$. The DOSY time and gradient pulse were set at 66.5 ms ($\Delta$) and 2 ms ($\delta$), respectively. All NMR data were processed using MestReNova 11.0.4 software.

Statistics: All results were expressed as mean±standard deviation (SD) unless specified otherwise and analyzed using GraphPad Prism 9.1 (GraphPad Software Inc., La Jolla, CA, USA).

Example 1. Selective Adsorption of Copolymer to Interfaces in mAb Formulations

To synthesize MoNi, reversible addition fragmentation transfer (RAFT) controlled radical polymerization was employed. The polymer was generated with a reactive trithiocarbonate chain transfer agent (CTA) attached at the Z terminus of the polymer following polymerization (denoted MoNi-CTA). The CTA moiety was removed from the MoNi-CTA copolymer to produce the MoNi excipient before utilization in subsequent assays to ensure both chemical stability and biological inertness (FIG. 2, Panel A-Panel D).

Figure 2:
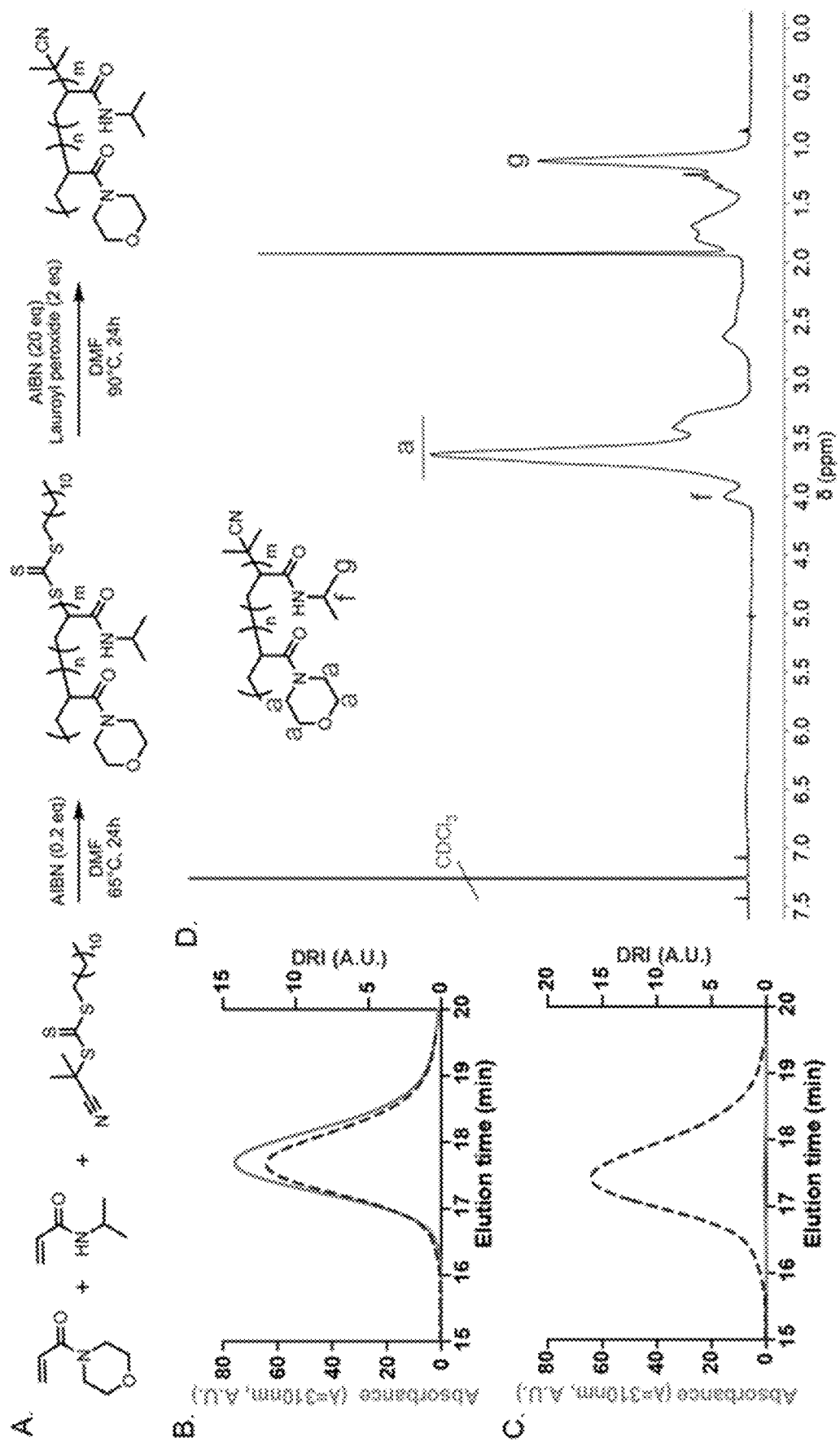
FIG. 2 is a set of schematics and graphs showing the synthesis and characterization of MoNi copolymer excipient. (Panel A) Synthetic scheme for the synthesis of poly (acryloylmorpholine-co-N-isopropylacrylamide) (MoNi). Size exclusion chromatography (SEC) characterization of the (Panel B) MoNi-CTA intermediate and (Panel C) MoNi demonstrated that the CTA is completely removed in the second step of the synthesis, yielding a chemically and physically stable copolymer. (Panel D) $^1$H-NMR characterization of MoNi. (Panel E) Comparison of cytotoxicity of MoNi, Polysorbate 80 (PS80), and Pluronic L61. (Panel F) DLS characterization of MoNi in solution at various concentrations demonstrated that the MoNi copolymer does not exhibit critical micelle concentration (CMC) behavior even at high concentrations. (Panel G) Comparison of reported CMC values for PS80 and Pluronic L61.
Figure 2:
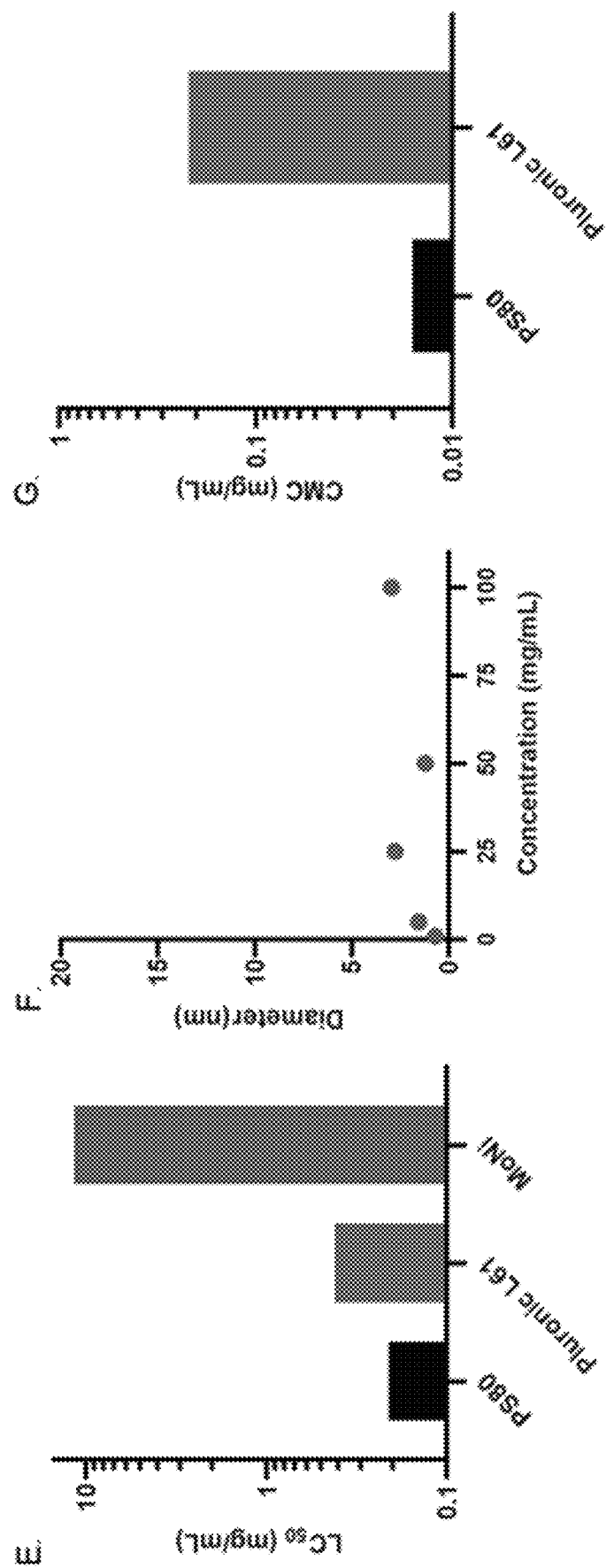

Reported values for the concentration whereby 50% of cells are killed in vitro, a parameter called the $LC_{50}$, were compared, and showed that MoNi is biocompatible and over 100-fold less cytotoxic than common commercial surfactant excipients such as Polysorbate 80 (PS80) and Pluronic L61 (FIG. 2, Panel E). Maikawa et al., *Biomacromolecules* 22(8):3386-95 (2021); Arechabala et al., *Journal of Applied Toxicology* 19(3):163-65 (1999); Demina et al., *Biomacromolecules* 15(7):2672-81 (2014).

The MoNi copolymer excipient was synthesized at molecular weights well below the glomerular filtration threshold to ensure that they are rapidly excreted following administration in the body without bioaccumulation. Further, determination of MoNi's critical micelle concentration (CMC) was attempted by performing dynamic light scattering (DLS) analysis on a dilution series of MoNi from 100 to 1 mg/mL (FIG. 2, Panel F). In these assays, the MoNi excipient did not form micelles or aggregates within the concentration range assessed. This behavior was unique compared to the common commercial surfactant excipients PS80 and Pluronic L61, which exhibit CMC values well below 1 mg/mL (FIG. 2, Panel G). Chou et al., *J. Pharm. Sci.* 94(6):1368-81 (2005); Carvalho et al., *International Journal of Pharmaceutics* 602:120635 (2021). Notably, most surfactants are toxic in their micellular state, suggesting that the significantly lower cytotoxicity of MoNi may relate to the fact that it does not exhibit self-assembly into micelles within formulation-relevant concentrations, contrasting its commercial counterparts. Demina, et al., *Biomacromolecules* 15(7):2672-81 (2014).

Whether MoNi preferentially adsorbs to the air-water interface was tested. Time-resolved surface tension experiments were conducted with formulations of the anti-HIV bnAb PGT121, a promising candidate for passive immunization against HIV targeting the well-conserved V1/V2 glycan on the gp120 surface glycoprotein. Patel et al., *J. Pharm. Sci.* 107(12):2969-82 (2018); Stephenson et al., *Nature Medicine* 27:1718-24 (2021). Formulations of PGT121 (20 mM acetate buffer, pH-5.2) with MoNi (0.01 wt %) exhibited lower surface tension values compared to PGT121 alone (53 mN/m and 62 mN/m, respectively; FIG. 3, Panel A). The lower surface tension observed for the PGT121 formulation comprising MoNi suggested that there were more species packed at the interface in this formulation than in the formulation with only PGT121, indicating that MoNi was preferentially adsorbing to the interface at higher levels. Notably, the surface tension of both a formulation of MoNi only in buffer and a formulation of PGT121 and MoNi were found to be identical (FIG. 3, Panel A), indicating that the air-water interface was indeed dominated by MoNi at these concentrations. These results suggested that MoNi preferentially adsorbed to the air-water interface, precluding mAb adsorption.

To further characterize the effects of MoNi on the formulation of PGT121 the interfacial viscoelasticity of these formulations was probed via interfacial shear rheology measurements. These measurements revealed that addition of MoNi to PGT121 formulations reduced the interfacial complex viscosity by 3-fold (from ~0.3 Pa·s·m to ~0.1 Pa·s·m$^1$; FIG. 3, Panel B). The high interfacial complex viscosity of the PGT121 formulation without MoNi suggested that protein interactions at the interface were indeed leading to the formation of a gel-like skin at the interface. Consequently, the significant reduction in interfacial complex viscosity upon addition of MoNi indicated that the copolymer excipient reduced interfacial interactions of PGT121, commensurate with the surface tension measurements discussed above that showed that the mAbs were precluded from adsorbing to the interfaces.

Figure 4:
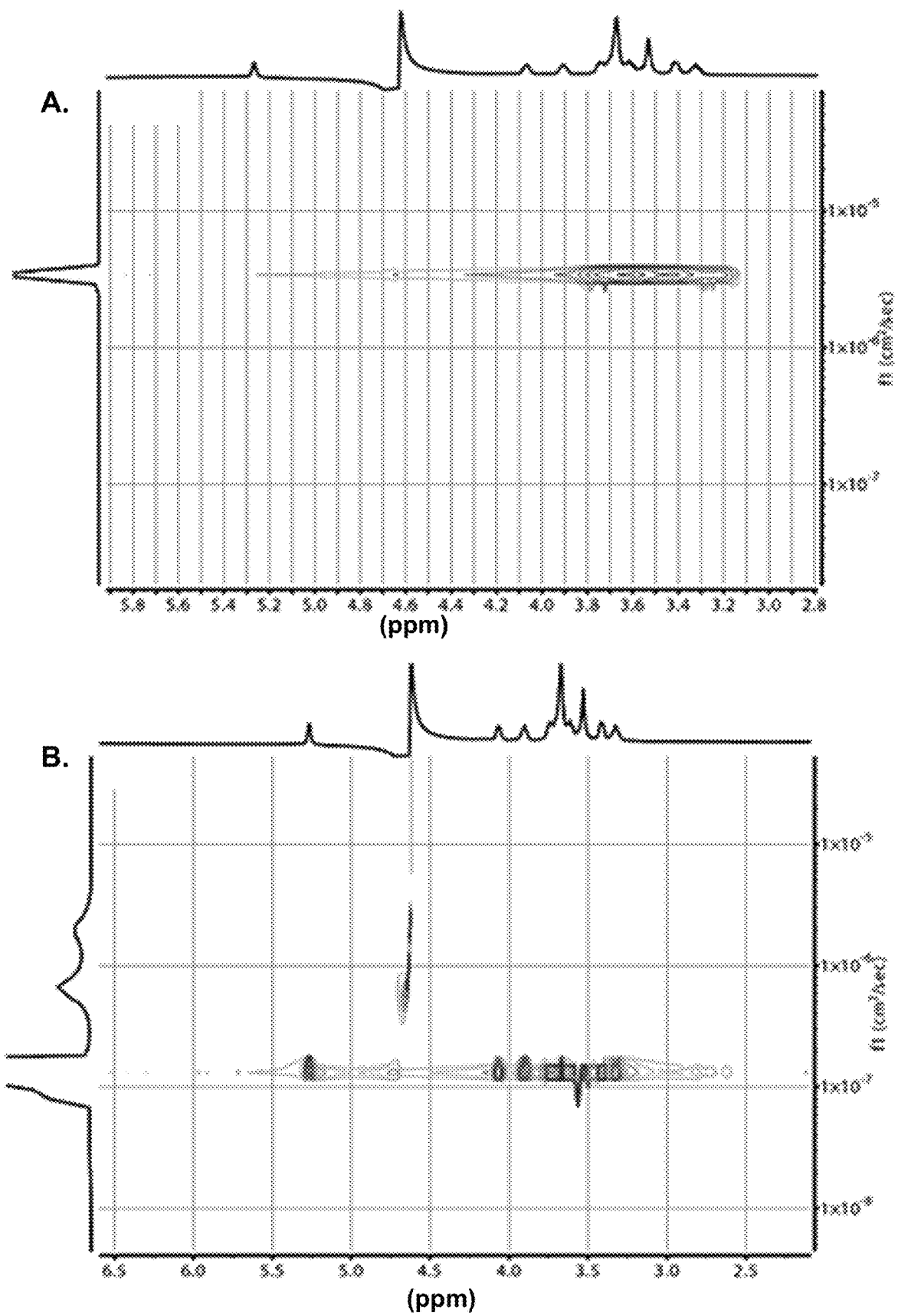
FIG. 4 is a set of diffusion ordered spectroscopy (DOSY) nuclear magnetic resonance (NMR) spectra of (Panel A) MoNi alone (0.1 mg/mL), (Panel B) PGT121 alone (0.2 mg/mL), and (Panel C) co-formulation of PGT121 and MoNi at 0.2 mg/mL and 0.1 mg/mL, respectively.
Figure 4:
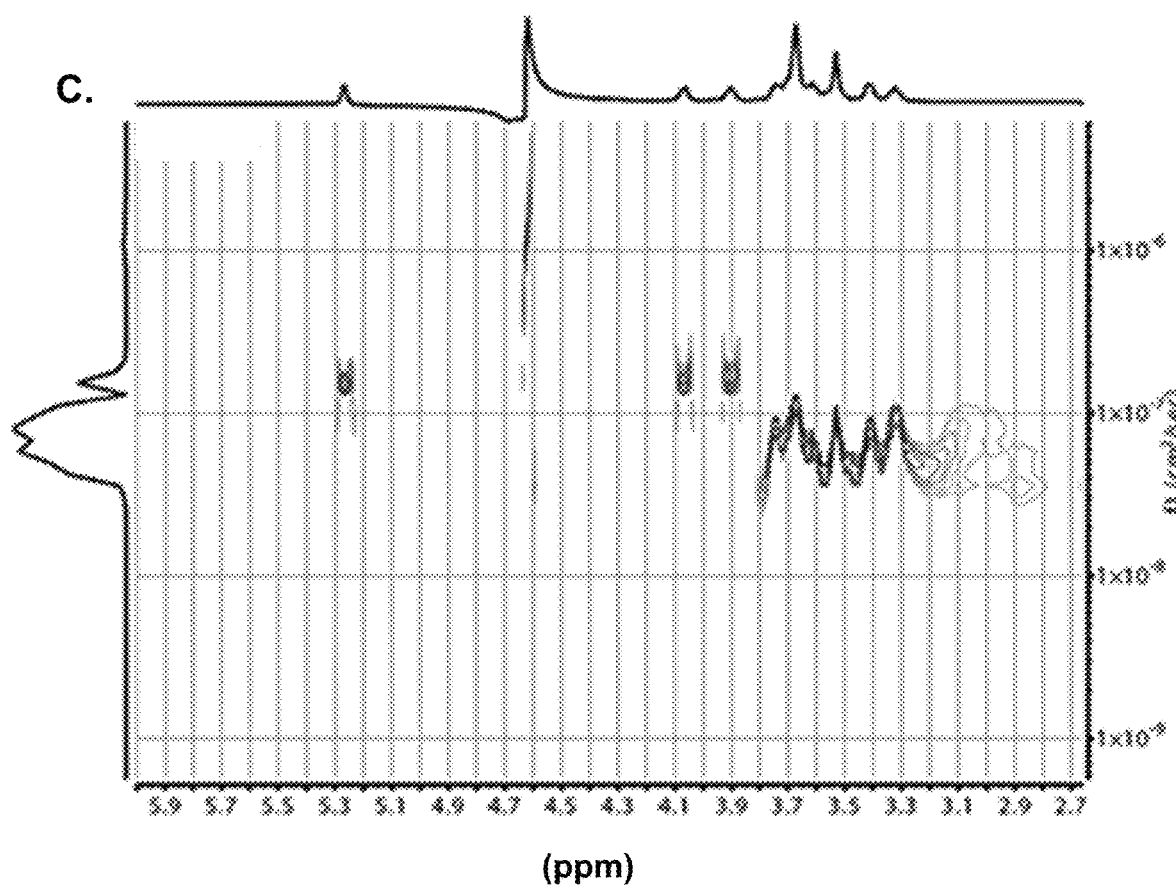

Whether MoNi interacted with the mAbs in the bulk was also determined using diffusion ordered spectroscopy (DOSY), a well-established NMR technique that provides direct evaluation of the diffusion behavior of different species in solution. As shown in FIG. 4, Panel A-Panel C, PGT121 mAb and MoNi exhibited distinct diffusion behavior, suggesting that the two species did not interact in the bulk. These results further indicate that MoNi acts to stabilize protein cargo by preventing interfacial aggregation.

Whether formulations with mAb concentrations greater than 100 mg/mL were easily injectable under clinically relevant injection conditions was determined. The viscosity of high-concentration PGT121 (119±7 mg/mL) solutions with and without MoNi (10 mg/mL) was at shear rates that are typically achieved during injection through a standard syringe and needle geometry and flow rate. Addition of MoNi at this concentration did not alter the injection viscosity of the formulation, and both formulations exhibited sufficiently low viscosities to be easily injected (FIG. 3, Panel C).

Example 2. Copolymer Stabilization of mAb Formulations in Stressed-Aging Assays

Figure 5:
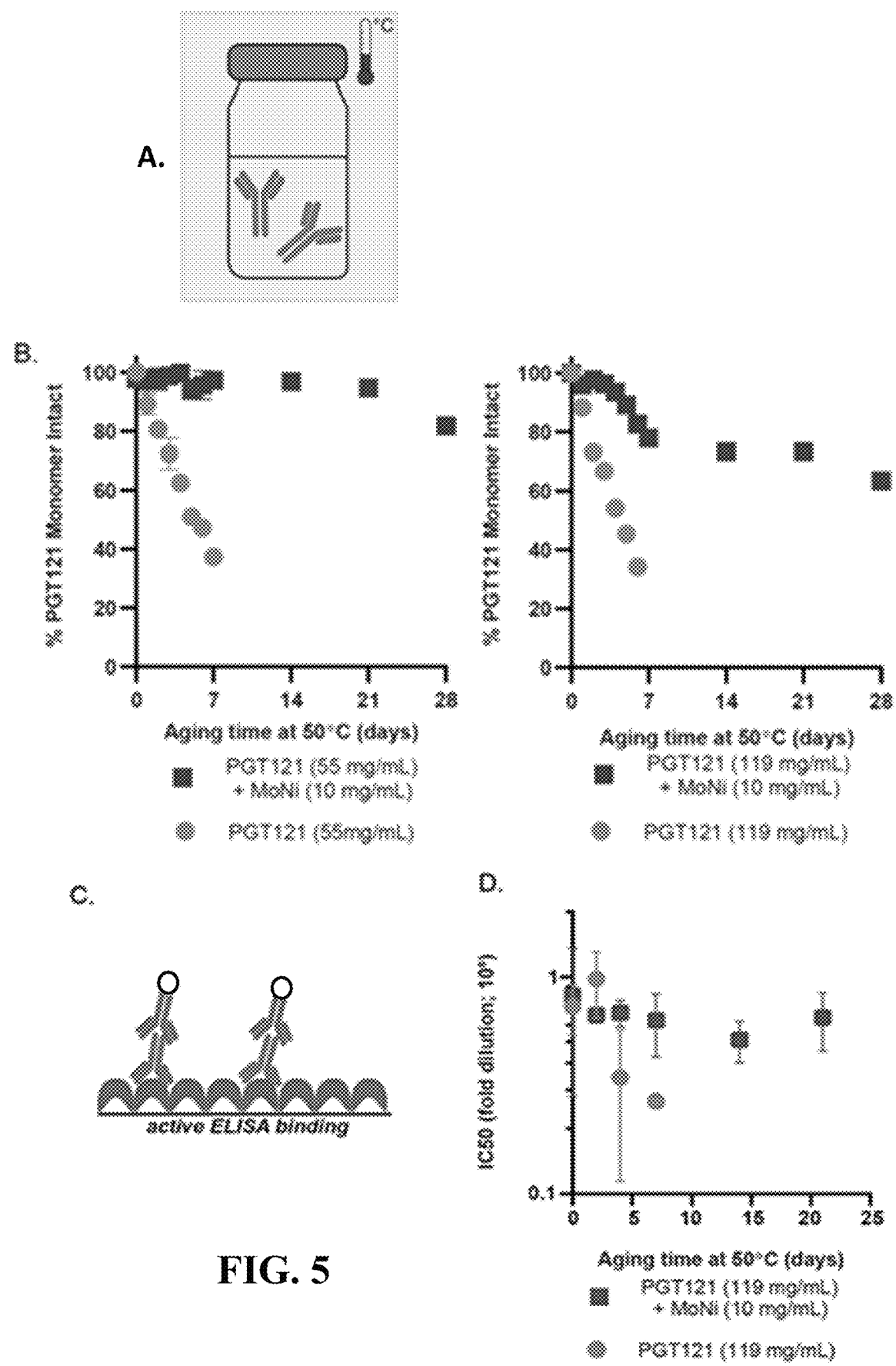
FIG. 5 is a set of schematics and graphs showing stabilization by MoNi of PGT121. (Panel A) Schematic of accelerated aging, whereby formulations are packaged in glass vials, agitated, and heated. (Panel B) Percent monomeric composition of aged samples determined via GPC. (Panel C) Schematic of assaying epitope binding via ELISA. (Panel D) Half maximal inhibitory concentrations ($IC_{50}$) of aged formulations with and without MoNi. Samples assayed in duplicate.
Figure 8:
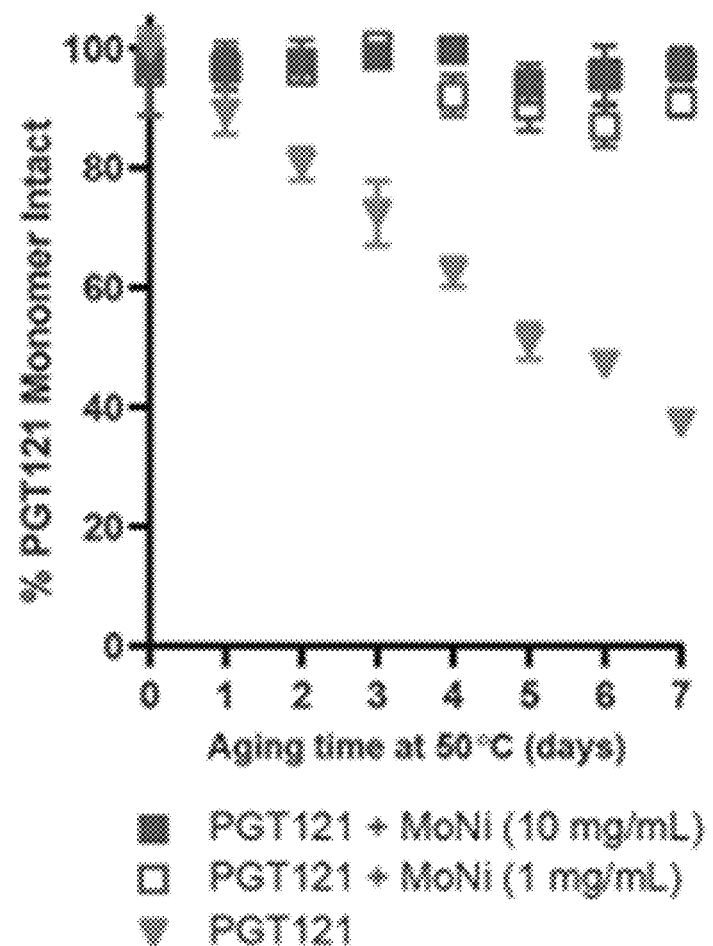
FIG. 8 is a graph showing percent monomeric composition of aged 55 mg/mL samples of PGT121 with or without MoNi determined via SEC.
Figure 9:
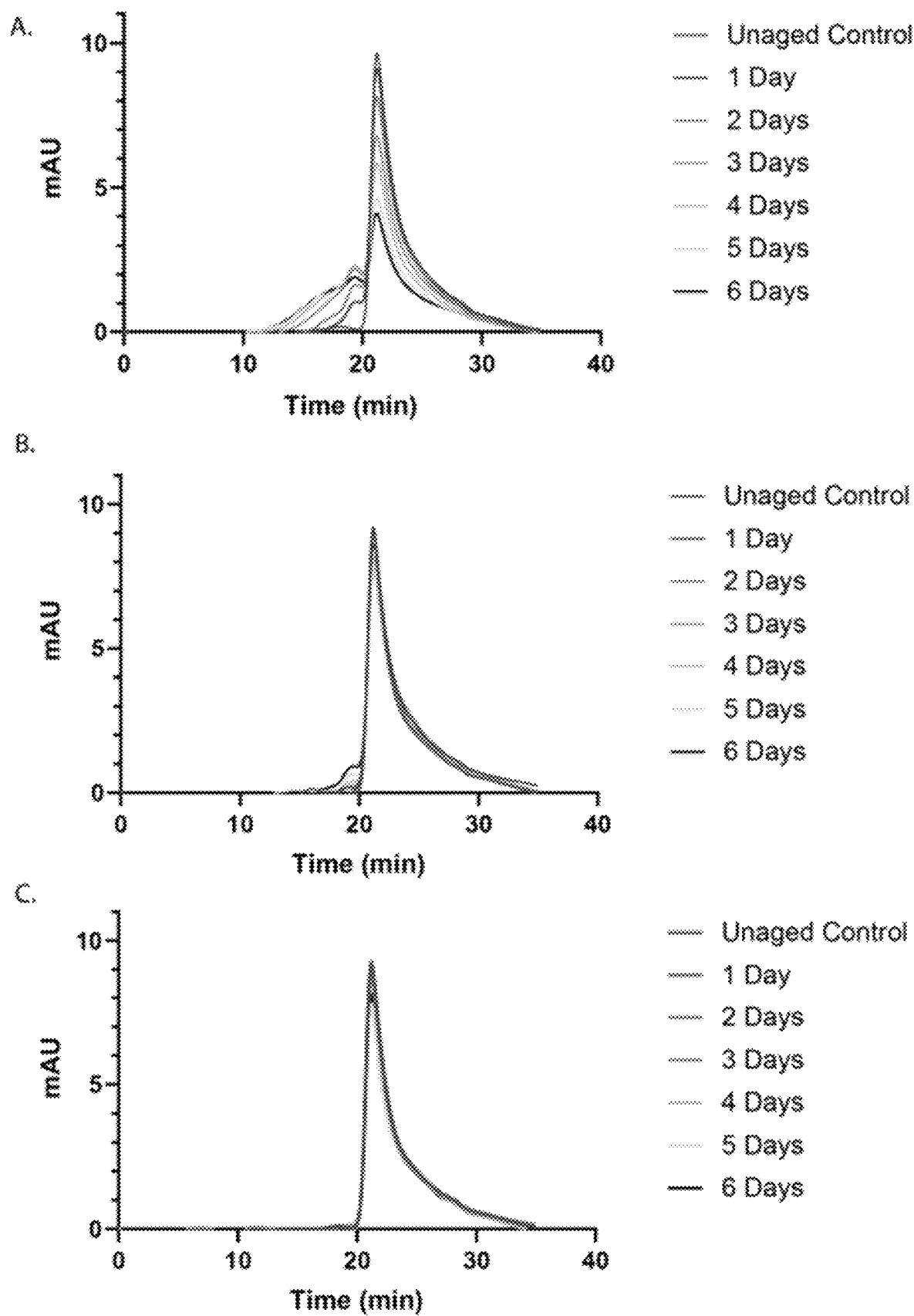
FIG. 9 is a set of graphs showing representative SEC chromatographs of PGT121 with or without MoNi subject to stressed aging conditions over six days. (Panel A) SEC chromatograph of PGT121 with no MoNi. (Panel B) SEC chromatograph of PGT121 with 1 mg/mL MoNi. (Panel C) SEC chromatograph of PGT121 with 10 mg/mL MoNi.

Accelerated aging assays were conducted. Initially, a stock PGT121 formulation at 55.5 mg/mL (20 nM acetate, 9 wt % sucrose, 0.01 wt % PS80, pH ~5.0) with MoNi (1 mg/mL, and 10 mg/mg) were compared. These formulations, including a control containing only the stock formulation of PGT121, were packaged in glass vials and subjected to accelerated aging (constant agitation at 50° C.). The monomeric mAb content in the formulations was monitored over 1 week (7 days) with size exclusion chromatography (SEC). While formulations containing MoNi at either concentration resulted in greater preservation of monomeric PGT121 over 7 days than in the control formulation without MoNi, the sample containing 10 mg/mL MoNi exhibited the best stability. (FIG. 8). Next, a stock PGT121 formulation at 55.5 mg/mL (20 mM acetate, 9 wt % sucrose, 0.01 wt % PS80, pH-5.0) was compared to a formulation concentrated more than 2-fold at 119±7 mg/mL (denoted herein as high concentration). These formulations with and without MoNi (10 mg/mL) were then packaged in glass vials and subjected to accelerated aging (constant agitation at 50° C.; FIG. 5, Panel A). The monomeric mAb content in these formulations was monitored over four weeks with size exclusion chromatography (SEC; FIG. 5, Panel B). Within 5 days, both the stock and high-concentration PGT121 formulations had lost more than 50% of their monomeric mAb content, indicating significant aggregation of the protein. The loss of monomeric PGT121 and formation of aggregates over 6 days is shown in representative SEC chromatograms of FIG. 9, panels A-C, where panel A is the representative SEC chromatogram for PGT121 with no MoNi; panel B is the representative SEC chromatogram for PGT121 with 1 mg/mL MoNi; and panel C is the representative SEC chromatogram for PGT121 with 10 mg/mL MoNi.

By day 7, both formulations had macroscopically aggregated, becoming visibly opaque. In contrast, the stock PGT121 formulation including MoNi maintained greater than 95% monomeric mAb content through three weeks of continuous stressed aging (FIG. 5, Panel B). While the high-concentration sample comprising MoNi exhibited a small initial decrease in monomer mAb content over the first week of stressed aging, likely arising from the concentration process, this formulation maintained near 70% monomer mAb content over the same three-week period (FIG. 5, Panel B).

Whether binding epitope activity (as a proxy for therapeutic efficacy) was preserved through continuous stressed aging was determined. An enzyme-linked immunosorbent assay (ELISA) was used to determine whether samples subjected to stressed aging retained binding activity, and thus conformational fidelity, in both their Fab and Fc domains (FIG. 5, Panel C). Half maximal inhibitory concentrations ($IC_{50}$) were used to compare the functional potency of the high-concentration formulations with and without MoNi (10 mg/mL) subjected to stressed aging. In the absence of MoNi, the PGT121 mAbs rapidly lost functionality, losing more than 65% of their potency after just five days of stressed aging (FIG. 5, Panel E). In contrast, the addition of MoNi significantly enhanced formulation stability and the PGT121 mAbs retained more than 75% of their original potency through 21 days of continuous stressed aging.

Taken together, these results indicate that the addition of the MoNi excipient to high-concentration mAb formulations conferred a substantial stability benefit by precluding mAb adsorption to the interfaces, thereby preventing aggregation events and maintaining binding activity under accelerated aging conditions.

Figure 6:
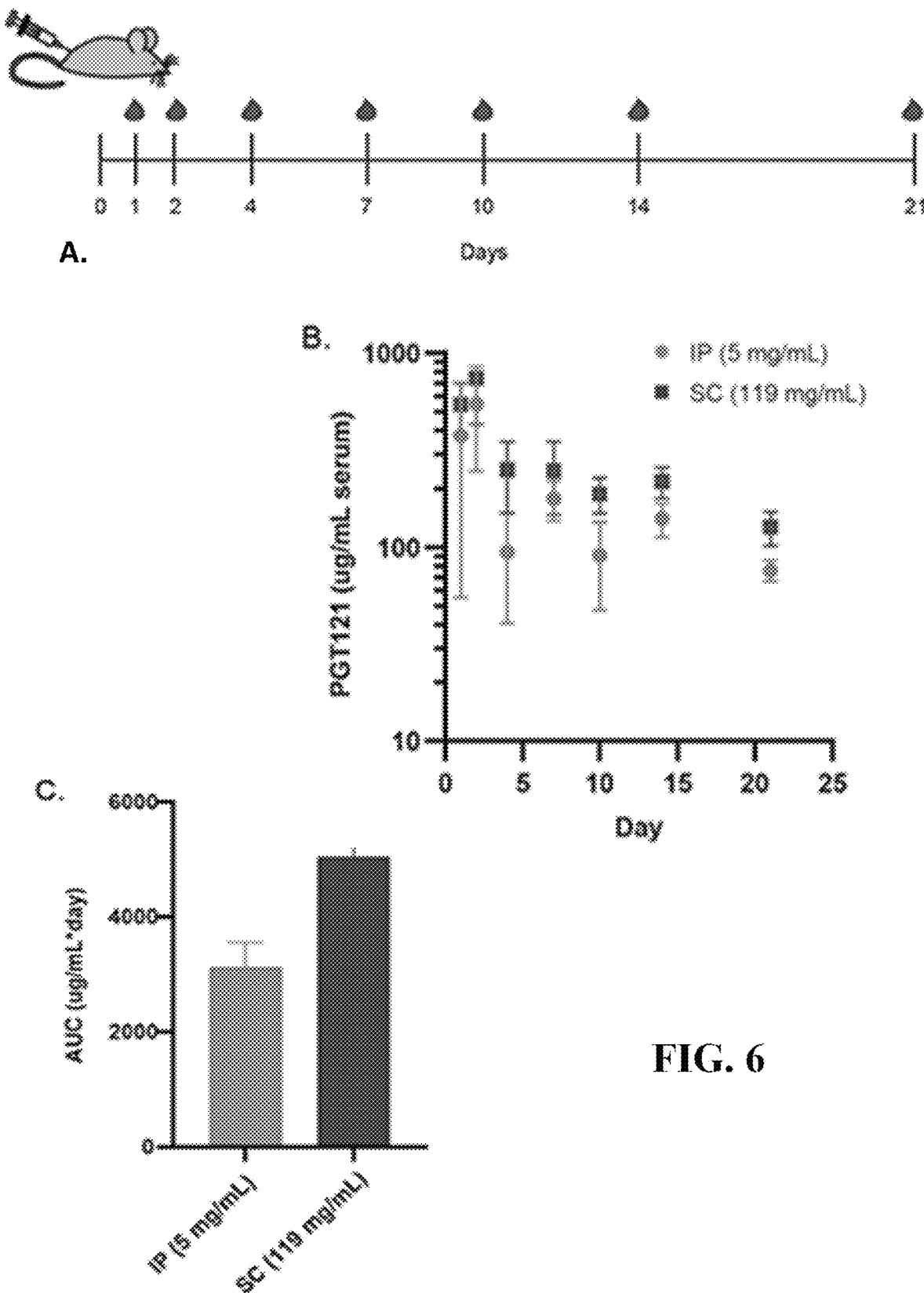
FIG. 6 is a set of schematics and graphs showing pharmacokinetics of a MoNi-stabilized PGT121 formulation. (Panel A) Experimental scheme reporting injection dosing and blood collection timeline in hFcRn mice used for comparing an IV administration of a low-concentration PGT121 (5 mg/mL) formulation and a SC administration of a MoNi-stabilized high-concentration PGT121 (119 mg/mL) formulation. (Panel B) Serum concentration of PGT121 over time, as determined by ELISA (n=6/group). (Panel C) Area under the curve analysis of ELISA data (n=6/group).

Example 3. Pharmacokinetic Profile of Copolymer-Stabilized High-Concentration PFT121 Formulation Whether MoNi functions as an inactive ingredient was determined through a pharmacokinetic study in rodents. 1.5 mg of PGT121 was administered to transgenic SCID mice with humanized FcRn receptors (n=6/group; B6.Cg-Fcgrt$^{tm1Dcr}$ Prkdc$^{scid}$ Tg[FCGRT]32Dcr/DcrJ; Jackson Labs No. 018441) via either SC injection of 15 μL of MoNi-stabilized high-concentration PGT121 (119 mg/mL) or IP injection of 300 μL of low concentration PGT121 (5 mg/mL). Serum was collected for three weeks post administration to be analyzed for systemic PGT121 concentration via ELISA (FIG. 6, Panel A-Panel B).

Figure 7:
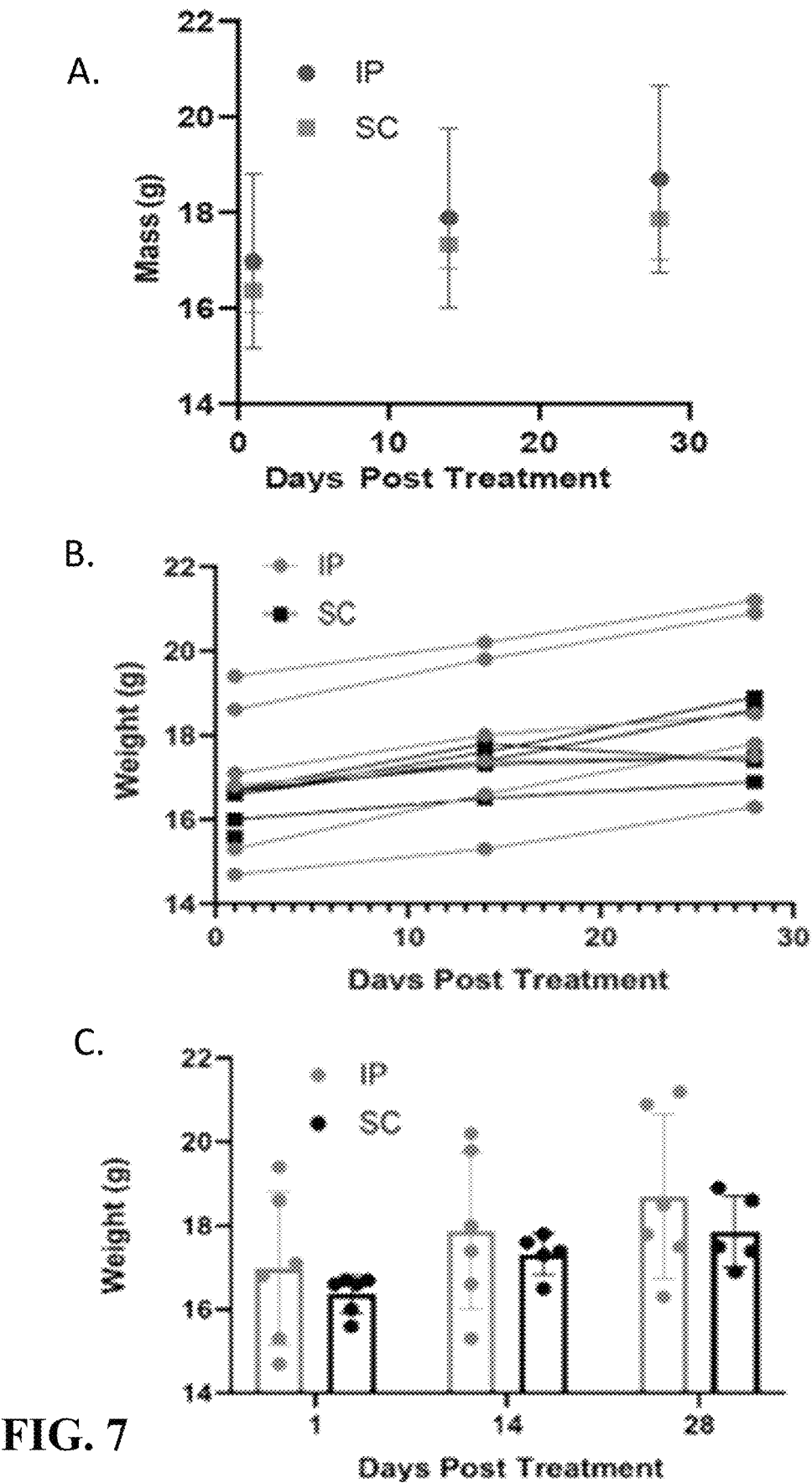
FIG. 7 (Panels A-C) is a set of graphs showing mouse weight over time post-treatment.

Quantification of serum concentration over time as well as total PGT121 exposure (area-under-the-curve; AUC) demonstrated comparable pharmacokinetics and bioavailability between the two routes of administration and formulations (FIG. 6, Panel C). No significant therapeutic difference was observed in terms of serum titer or bioavailability of PGT121 when administered in a MoNi-stabilized, high-concentration formulation. Moreover, no acute weight loss (a common metric for treatment related toxicity) was observed, further showing MoNi's biocompatibility and tolerability (FIG. 7, panels A-C).

The addition of MoNi to high-concentration PGT121 mAb formulations significantly improved their stability without impacting pharmacokinetics, as would be required for development of clinically relevant SC formulations. These results demonstrated MoNi's remarkable usefulness as an excipient to address biopharmaceutical formulation challenges.

INCORPORATION BY REFERENCE

All publications, patents, patent applications, and other documents cited in this application, including U.S. Provisional Appl. No. 63/344,927 and published international application no. WO 2021/211976, are hereby incorporated by reference in their entireties for all purposes to the same extent as if each individual publication, patent, patent application, or other document were individually indicated to be incorporated by reference for all purposes.

The invention claimed is:

1. A composition comprising:
    a polyacrylamide-based copolymer comprising:
    a water-soluble carrier monomer selected from N-(3-methoxypropyl)acrylamide (MPAM), 4-acryloylmorpholine (MORPH), N,N-dimethylacrylamide (DMA), N-hydroxyethyl acrylamide (HEAM), acrylamide (AM), and combinations thereof; and
    a functional dopant monomer selected from N-[tris(hydroxymethyl)-methyl]acrylamide (TRI), 2-acrylamido-2-methylpropane sulfonic acid (AMP), (3-acrylamidopropyl)trimethylammonium chloride (TMA), N-isopropylacrylamide (NIP), N—N-diethylacrylamide (DEA), N-tert-butylacrylamide (TBA), N-phenylacrylamide (PHE), and combinations thereof; and
    an antibody.

2. The composition of claim 1, wherein the water-soluble carrier monomer is selected from MORPH, MPAM, and combinations thereof.

3. The composition of claim 1, wherein the functional dopant monomer is selected from AMP, TMA, TBA, PHE, and combinations thereof.

4. The composition of claim 1, wherein the functional dopant monomer is selected from DEA, PHE, NIP, and combinations thereof.

5. The composition of claim 1, wherein the functional dopant monomer comprises TRI.

6. The composition of claim 1, wherein the functional dopant monomer comprises PHE.

7. The composition of claim 1, wherein the functional dopant monomer comprises NIP.

8. The composition of claim 1, wherein the functional dopant monomer comprises DEA.

9. The composition of claim 1, wherein:
the water-soluble carrier monomer is selected from MPAM, MORPH, and combinations thereof; and
the functional dopant monomer is selected from NIP, PHE, and combinations thereof.

10. The composition of claim 1, wherein:
the water-soluble carrier monomer is selected from MPAM, MORPH, and combinations thereof; and
the functional dopant monomer is selected from AMP, TMA, TBA, PHE, and combinations thereof.

11. The composition of claim 1, wherein the water-soluble carrier monomer is MPAM, and the functional dopant monomer is PHE.

12. The composition of claim 1, wherein the water-soluble carrier monomer is MORPH, and the functional dopant monomer is PHE.

13. The composition of claim 1, wherein the water-soluble carrier monomer is MORPH, and the functional dopant monomer is NIP.

14. The composition of claim 1, wherein the copolymer comprises:
70 wt % to 98 wt % of the water-soluble carrier monomer; and
2 wt % to 30 wt % of the functional dopant monomer.

15. The composition of claim 1, wherein the copolymer comprises:
70 wt % to 85 wt % of MORPH; and
15 wt % to 30 wt % of NIP.

16. The composition of claim 1, comprising 0.1 wt % to 10 wt % of the copolymer, wherein a degree of polymerization of the copolymer is 10 to 500, and wherein a number-average molecular weight of the copolymer is 2,000 g/mol to 10,000 g/mol.

17. The composition of claim 1, comprising 5 wt % or more of the antibody.

18. The composition of claim 17, comprising 10 wt % or more of the antibody.

19. The composition of claim 1, comprising 2.5 wt % to 20 wt % of the antibody.

20. The composition of claim 1, wherein the antibody has a molecular weight of 100 kDa to 200 kDa.

21. The composition of claim 1, wherein the antibody is a monoclonal antibody.

22. The composition of claim 1, wherein the antibody is selected from a chimeric antibody, bispecific antibody, full-length antibody, antibody fragment, and an antibody-drug conjugate.

23. The composition of claim 1, comprising:
0.1 wt % to 10 wt % of a polyacrylamide-based copolymer comprising:
70 wt % to 98 wt % of a water-soluble carrier monomer selected from MPAM, MORPH, DMA, HEAM, AM, and combinations thereof; and
2 wt % to 30 wt % of a functional dopant monomer selected from TRI, AMP, TMA, NIP, TBA, PHE, and combinations thereof; and
5 wt % or more of the antibody.

24. The composition of claim 23, comprising 10 wt % or more of the antibody.

25. The composition of claim 23, wherein:
the water-soluble carrier monomer is selected from MPAM, MORPH, and combinations thereof; and
the functional dopant monomer is selected from NIP, PHE, and combinations thereof.

26. The composition of claim 25, wherein:
the water-soluble carrier monomer is MORPH; and
the functional dopant monomer is NIP.

27. The composition of claim 23, further comprising:
0.001 wt % to 0.5 wt % of a surfactant;
0.1 wt % to 25 wt % of a stabilizer; and
a buffer,
wherein the composition is aqueous and has a pH of 3 to 7.5.

28. The composition of claim 1, wherein the composition is formulated for subcutaneous administration.

29. A method of administering an antibody to a subject in need thereof, comprising injecting the subject with a therapeutically effective amount of a composition according to claim 1.

30. The composition of claim 1, wherein the composition comprises a suspension of particles in a liquid carrier, wherein the particles comprise the polyacrylamide-based copolymer and the antibody.

* * * * *